US009808222B2

(12) United States Patent
Moore et al.

(10) Patent No.: US 9,808,222 B2
(45) Date of Patent: Nov. 7, 2017

(54) INTRAVASCULAR ULTRASOUND SYSTEM FOR CO-REGISTERED IMAGING

(75) Inventors: Thomas C. Moore, Livermore, CA (US); Kendall R. Waters, Livermore, CA (US); J. Steve Reynolds, Palo Alto, CA (US); Duc H. Lam, San Jose, CA (US); Donald Masters, San Diego, CA (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 945 days.

(21) Appl. No.: 12/902,460

(22) Filed: Oct. 12, 2010

(65) Prior Publication Data
US 2011/0087104 A1   Apr. 14, 2011

Related U.S. Application Data

(60) Provisional application No. 61/250,781, filed on Oct. 12, 2009, provisional application No. 61/256,543, filed on Oct. 30, 2009.

(51) Int. Cl.
*A61B 8/00*       (2006.01)
*A61B 8/12*       (2006.01)
(Continued)

(52) U.S. Cl.
CPC .......... *A61B 8/4461* (2013.01); *A61B 8/0891* (2013.01); *A61B 8/12* (2013.01);
(Continued)

(58) Field of Classification Search
CPC ....... A61B 5/06; A61B 8/0833; A61B 8/0891; A61B 8/12; A61B 8/445; A61B 8/4461;
(Continued)

(56) References Cited

U.S. PATENT DOCUMENTS

| 4,347,443 A | 8/1982 | Whitney |
| 4,850,363 A | 7/1989 | Yanagawa |

(Continued)

FOREIGN PATENT DOCUMENTS

| CN | 101208045 A | 6/2008 |
| EP | 0346889 A1 | 12/1989 |

(Continued)

OTHER PUBLICATIONS

Extended European Search Report dated Apr. 17, 2013 for EP Application No. 10823924.5, 6 pages.

(Continued)

*Primary Examiner* — Amanda Lauritzen Moher
(74) *Attorney, Agent, or Firm* — Fredrikson & Byron, P.A.

(57) ABSTRACT

An intravascular ultrasound imaging system with a catheter having an elongated body having a distal end and an imaging core arranged to be inserted into the elongated body. The imaging core is arranged to transmit ultrasonic energy pulses and to receive reflected ultrasonic energy pulses. The system further includes an imaging engine coupled to the imaging core and arranged to provide the imaging core with energy pulses to cause the imaging core to transmit the ultrasonic energy pulses. The energy pulses are arranged in repeated sequences and the energy pulses of each sequence have varying characteristics. The reflected pulses may be processed to provide a composite image of images resulting from each different characteristic.

11 Claims, 23 Drawing Sheets

(51) Int. Cl.
*G01S 7/52* (2006.01)
*A61B 8/08* (2006.01)
*G01S 15/10* (2006.01)
*G01S 15/89* (2006.01)
*A61B 5/06* (2006.01)

(52) U.S. Cl.
CPC .............. *A61B 8/445* (2013.01); *A61B 8/463* (2013.01); *G01S 7/52071* (2013.01); *G01S 7/52074* (2013.01); *A61B 5/06* (2013.01); *A61B 8/0833* (2013.01); *G01S 15/102* (2013.01); *G01S 15/8952* (2013.01)

(58) Field of Classification Search
CPC ... A61B 8/463; G01S 15/102; G01S 15/8952; G01S 7/52071; G01S 7/52074
See application file for complete search history.

(56) References Cited

U.S. PATENT DOCUMENTS

| | | | |
|---|---|---|---|
| 4,860,758 A | 8/1989 | Yanagawa et al. | |
| 4,949,310 A | 8/1990 | Smith et al. | |
| 5,070,734 A | 12/1991 | Kawabuchi et al. | |
| 5,131,396 A | 7/1992 | Ishiguro et al. | |
| 5,183,048 A | 2/1993 | Eberle | |
| 5,203,338 A | 4/1993 | Jang | |
| 5,363,849 A | 11/1994 | Suorsa et al. | |
| 5,396,285 A | 3/1995 | Hedberg et al. | |
| 5,462,057 A | 10/1995 | Hunt et al. | |
| 5,531,679 A | 7/1996 | Schulman et al. | |
| 5,690,115 A | 11/1997 | Feldman et al. | |
| 5,741,552 A | 4/1998 | Takayama et al. | |
| 5,833,615 A | 11/1998 | Wu et al. | |
| 5,848,969 A | 12/1998 | Panescu et al. | |
| 5,876,343 A * | 3/1999 | Teo | A61B 8/12 600/443 |
| 6,015,385 A | 1/2000 | Finger et al. | |
| 6,132,374 A | 10/2000 | Hossack et al. | |
| 6,139,501 A | 10/2000 | Roundhill et al. | |
| 6,154,572 A | 11/2000 | Chaddha | |
| 6,216,025 B1 | 4/2001 | Kruger | |
| 6,277,075 B1 | 8/2001 | Torp et al. | |
| 6,454,715 B2 * | 9/2002 | Teo | A61B 8/06 600/443 |
| 6,589,181 B2 | 7/2003 | Grunwald et al. | |
| 6,645,147 B1 | 11/2003 | Jackson et al. | |
| 7,194,294 B2 | 3/2007 | Panescu et al. | |
| 7,691,061 B2 | 4/2010 | Hirota | |
| 7,925,064 B2 | 4/2011 | Cloutier et al. | |
| 2001/0017941 A1 | 8/2001 | Chaddha | |
| 2001/0029336 A1 | 10/2001 | Ieo | |
| 2003/0063787 A1 * | 4/2003 | Natanzon | G01T 1/1615 382/131 |
| 2003/0078497 A1 * | 4/2003 | Ji et al. | 600/437 |
| 2003/0097069 A1 | 5/2003 | Avinash et al. | |
| 2003/0191392 A1 | 10/2003 | Haldeman | |
| 2003/0208123 A1 | 11/2003 | Panescu | |
| 2004/0030250 A1 | 2/2004 | Stewart | |
| 2004/0037164 A1 * | 2/2004 | Garlick et al. | 367/8 |
| 2004/0199047 A1 | 10/2004 | Taimisio et al. | |
| 2005/0215897 A1 | 9/2005 | Sakaguchi et al. | |
| 2005/0249391 A1 | 11/2005 | Kimmel et al. | |
| 2006/0253028 A1 | 11/2006 | Lam et al. | |
| 2007/0016068 A1 * | 1/2007 | Grunwald et al. | 600/468 |
| 2007/0036404 A1 | 2/2007 | Li | |
| 2007/0167710 A1 | 7/2007 | Unal et al. | |
| 2008/0015569 A1 * | 1/2008 | Saadat et al. | 606/41 |
| 2008/0031498 A1 | 2/2008 | Corcoran et al. | |
| 2008/0200815 A1 | 8/2008 | Van Der Sieen et al. | |
| 2009/0088830 A1 * | 4/2009 | Mohamed et al. | 623/1.11 |
| 2009/0284332 A1 | 11/2009 | Moore et al. | |
| 2010/0010344 A1 | 1/2010 | Ahn et al. | |
| 2010/0094127 A1 | 4/2010 | Xu | |
| 2010/0174190 A1 | 7/2010 | Hancock et al. | |
| 2010/0312109 A1 | 12/2010 | Satoh | |
| 2011/0071404 A1 | 3/2011 | Schmitt et al. | |
| 2011/0160586 A1 | 6/2011 | Li et al. | |
| 2012/0065511 A1 | 3/2012 | Jamello, III | |
| 2012/0123271 A1 | 5/2012 | Cai | |
| 2012/0170848 A1 | 7/2012 | Kemp et al. | |
| 2013/0109968 A1 | 5/2013 | Azuma | |
| 2013/0303907 A1 | 11/2013 | Corl | |
| 2013/0303910 A1 | 11/2013 | Hubbard et al. | |
| 2014/0180078 A1 | 6/2014 | Nair | |
| 2014/0276065 A1 * | 9/2014 | He | A61B 8/5207 600/445 |
| 2015/0099975 A1 | 4/2015 | Lam et al. | |
| 2015/0141832 A1 | 5/2015 | Yu et al. | |

FOREIGN PATENT DOCUMENTS

| | | |
|---|---|---|
| EP | 851241 A2 | 7/1998 |
| EP | 1387317 A1 | 2/2004 |
| EP | 1609423 A2 | 12/2005 |
| EP | 10823924.5 | 4/2011 |
| JP | 2009000522 | 1/1997 |
| JP | 2001333902 A | 12/2001 |
| JP | 2002530143 A | 9/2002 |
| JP | 2004180784 | 7/2004 |
| JP | 2006-014938 | 1/2006 |
| JP | 2007029520 A | 2/2007 |
| JP | 2007175542 A | 7/2007 |
| JP | 2007229015 A | 9/2007 |
| JP | 2008508970 A | 3/2008 |
| JP | 2008536638 A | 9/2008 |
| JP | 2009545406 A | 12/2009 |
| JP | 4648652 B2 | 3/2011 |
| JP | 2013507227 A | 3/2013 |
| WO | 0101864 A1 | 1/2001 |
| WO | WO2006015877 A1 | 2/2006 |
| WO | WO2006113857 A1 | 10/2006 |
| WO | 2006122001 A2 | 11/2006 |
| WO | 2007098209 A2 | 8/2007 |
| WO | 2008016992 A1 | 2/2008 |
| WO | 2008110013 A1 | 9/2008 |
| WO | 2011046903 A1 | 4/2011 |
| WO | 2014186268 A1 | 11/2014 |

OTHER PUBLICATIONS

Van Der Steen A.F.W. et al.: "IVUS Harmonic Imaging," Ultrasound Med BIOL; Ultrasound in Medicine and Biology 2000 Elsevier Science LTD, Exter, Engl, vol. 26, No. supp. 2, 2000, p. A90.

Foster, F. Stuart: "Transcuder Materials and Probe Construction," Ultrasound in Medicine and Biology, New York, NY, US, vol. 26, May 2000, pp. S2-S5.

Frijlink, M.E. et al.: "High Frequency Harmonic Imaging in Presence of Intravascular Stents," IEEE Ultrasonics Symposium (IEEE CAT. No. 03CH37476) Piscataway, NJ, USA, vol. 1, 2003, pp. 208-211.

U.S. Appl. No. 61/218,177, filed Jun. 18, 2009 titled Vector Domain Image Enhancement for Mechnically Rotating Imaging Catheters.

Dumane et al., "Use of Frequency Diversity and Nakagami Statistics in Ultrasonic Tissue Characterization," IEEE Transactions on Ultrasonics, Ferroelectrics, and Frequency Control, vol. 48, No. 5, Sep. 2001, pp. 1139-1146.

Garcia-Garcia et al., "Imaging of coronary atherosclerosis: intravascular ultrasound," European Heart Journal, vol. 3, 2010, pp. 2456-2469.

International Patent Application No. PCT/US2010/052258, International Search Report & Written Opinion dated May 18, 2011, 6 pages.

Seo et al., "Sidelobe Suppression in Ultrasound Imaging Using Dual Apodization with Cross-Correlation," IEEE Transactions on Ultrasonics, Ferroelectrics, and Frequency Control, vol. 55, No. 10, Oct. 2008, pp. 2198-2210.

Shankar et al., "Computer-Aided Classification of Breast Masses in Ultrasonic B-Scans Using a Multiparameter Approach," IEEE

(56) References Cited

OTHER PUBLICATIONS

Transactions on Ultrasonics, Ferroelectrics, and Frequency Control, vol. 50, No. 8, Aug. 2003, pp. 1002-1009.
Smith et al., "The Maltese Cross Processor: Speckle Reduction for Circular Transducers," Ultrasonic Imaging, vol. 10, No. 3, Jul. 1988, pp. 153-170.
Wang et al., "Optimizing the Beam Pattern of a Forward-Viewing Ring-Annular Ultrasound Array for Intravascular Imaging," IEEE Transactions on Ultrasonics, Ferroelectrics, and Frequency Control, vol. 49, No. 12, Dec. 2002, pp. 1652-1664.
Waters et al., "Development of a High-Definition Intravascular Ultrasound Imaging System and Catheter," IEEE International Ultrasonics Symposium Proceedings, Oct. 18, 2011, 4 pages.

* cited by examiner

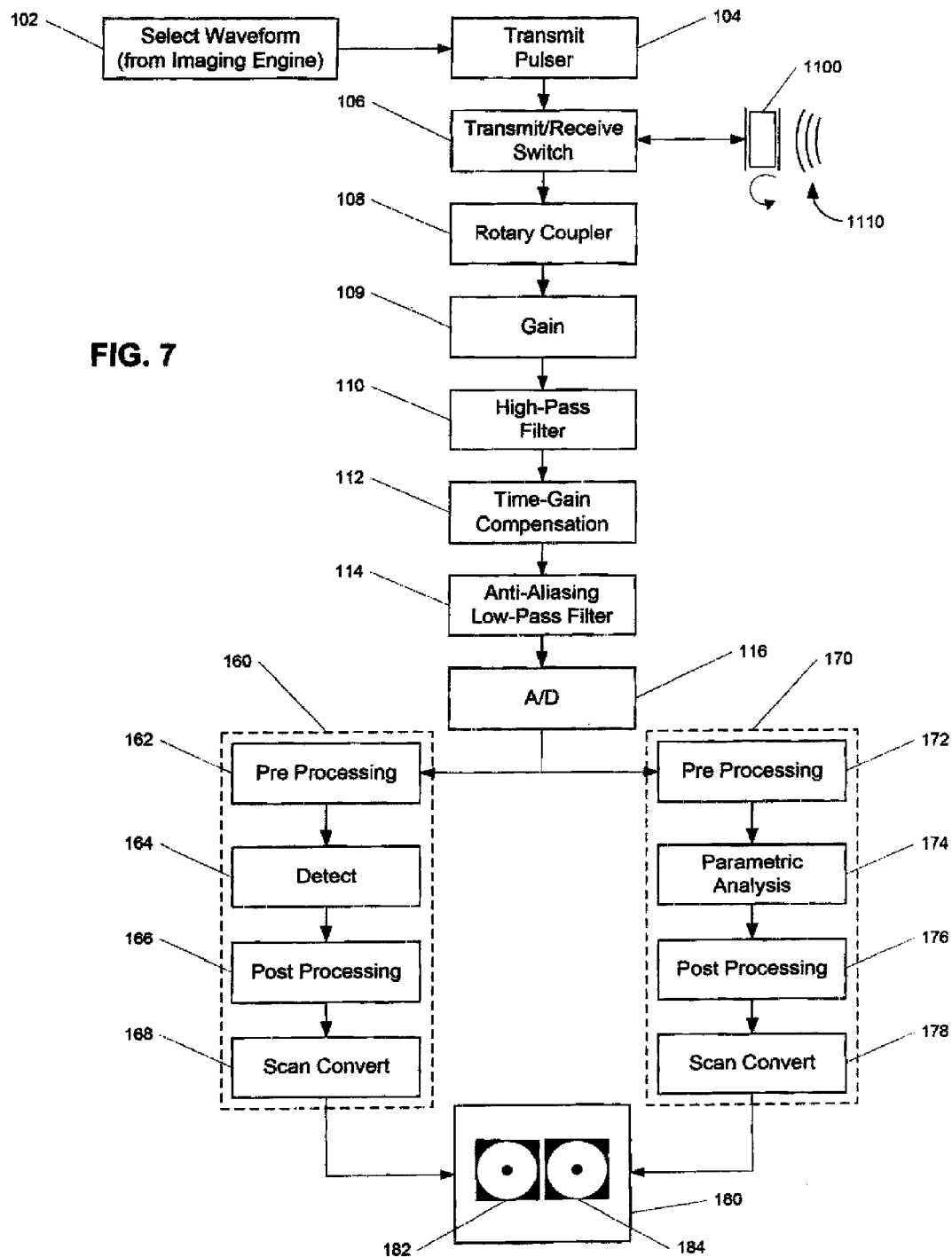

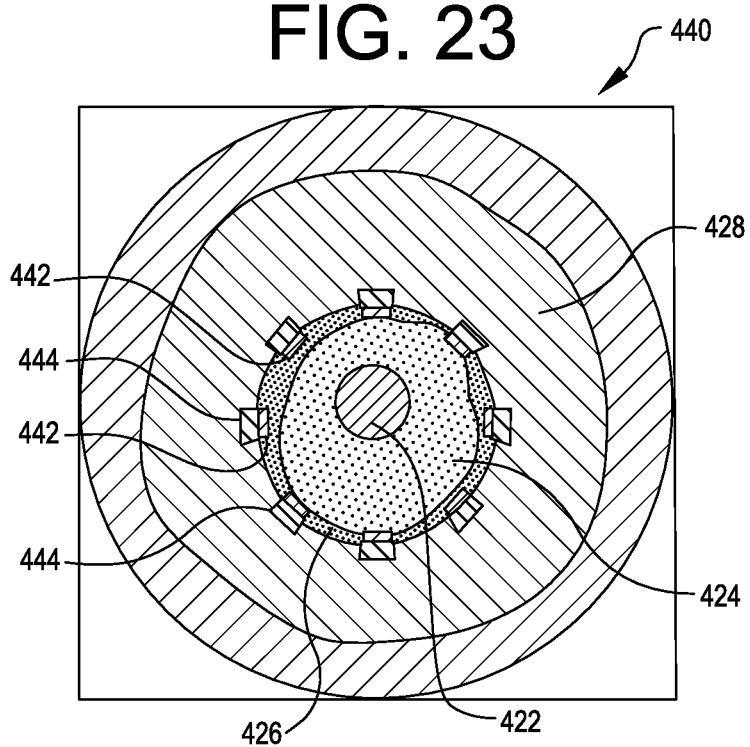
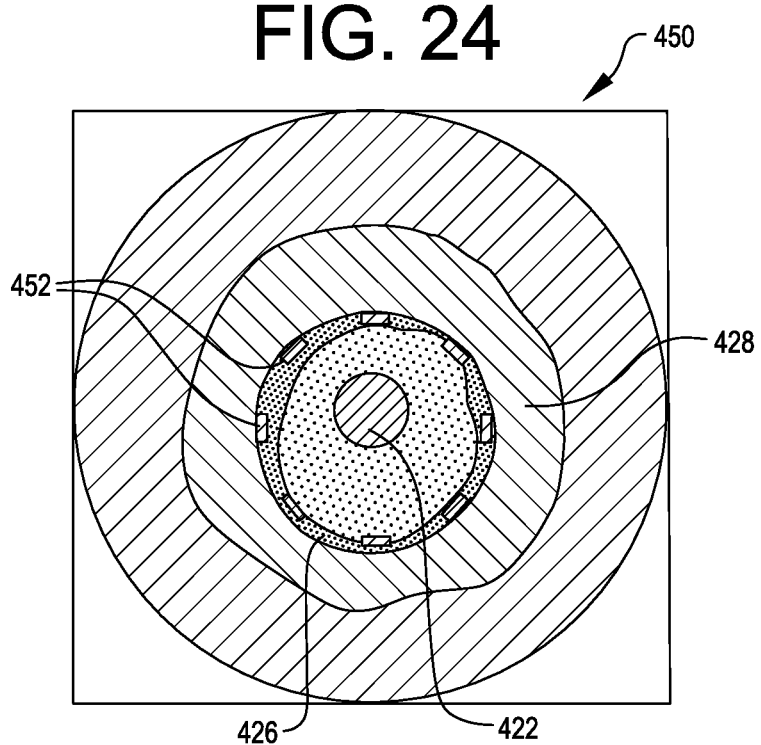

INTRAVASCULAR ULTRASOUND SYSTEM FOR CO-REGISTERED IMAGING

PRIORITY CLAIM

The present application claims the benefit of U.S. Provisional Patent Application Ser. No. 61/250,781, filed Oct. 12, 2009; the present application also claims the benefit of U.S. Provisional Patent Application Ser. No. 61/256,543, filed Oct. 30, 2009, all of the foregoing applications are incorporated herein by reference in their entireties.

BACKGROUND

The present invention generally relates to intravascular ultrasound (IVUS) imaging. The present invention more specifically relates to IVUS systems for co-registered imaging.

Intravascular ultrasound imaging is generally performed to guide and assess percutaneous coronary interventions, typically the placement of a bare-metal or drug-eluting stent. Other applications of IVUS imaging comprise further assessment of coronary artery disease.

Coronary stents generally have struts made of a metal, such as stainless steel or a cobalt chromium alloy. The metal stent struts provide a substantially larger reflected ultrasound signal than blood and soft tissue, such as neotissue grown over stent struts. The ability to detect and measure neotissue growth is particularly relevant for evaluating the stent healing process. Current commercially available IVUS systems have limited ability to detect early neotissue growth, because of a limited detectable range of reflected ultrasound signals.

Atherosclerotic lesions that are prone to rupture, so called vulnerable plaques, are of increasing interest to interventional cardiologists. One type of vulnerable plaque thought to be responsible for a large percentage of plaque ruptures is a thin-cap fibroatheroma wherein a thin (<65 µm) fibrous cap overlies a mechanically unstable lipid-rich or necrotic core. Current commercially available IVUS systems operate up to only 40 MHz and have axial resolutions that are limited to approximately 100 µm. Consequently, current commercially available IVUS systems cannot reliably detect vulnerable plaques.

It is generally necessary to increase the imaging frequency in order to improve spatial resolution. However, increased imaging frequency also leads to reduced contrast between blood and non-blood tissue that in turn makes difficult segmentation of the blood-filled lumen from the intimal plaque. Some automatic segmentation algorithms exploit the frequency-dependent ultrasound properties of blood and non-blood tissues as described for example in U.S. Pat. No. 5,876,343 by Teo. Real-time, automatic segmentation tools are often prone to errors which reduce their utility in clinical practice.

Multi-frequency imaging has been developed for transthoracic echocardiographic applications. U.S. Pat. No. 6,139,501 by Roundhill et al. describes a system that simultaneously displays two B-mode images of different imaging frequencies and bandwidths. However, this technique uses both fundamental and harmonic imaging techniques and relies upon non-linear propagation properties of tissue. Although harmonic imaging can potentially provide better spatial resolution, harmonic imaging performance in the near-field is limited. Further, harmonic IVUS imaging has not been found to be practically useful.

Multi-frequency IVUS imaging can also be achieved by use of multiple transducer imaging catheters. However, multiple transducers add complexity and cost to the disposable imaging catheter and the imaging system. The potential need to co-register the images from the separate transducers further complicates their practical use.

There exists a need for a technology that provides sufficient contrast resolution to guide percutaneous coronary interventions and sufficient contrast and spatial resolution to detect stent healing and vulnerable plaques. Further, it is desirable that such a technology does not require any co-registration step between multiple images. Still further, it is desirable that such a technology does not substantially increase system and catheter complexity and cost over existing commercial systems and catheters.

SUMMARY

The invention provides an intravascular ultrasound imaging system comprising a catheter having an elongated body having a distal end and an imaging core arranged to be inserted into the elongated body. The imaging core is arranged to transmit ultrasonic energy pulses and to receive reflected ultrasonic energy pulses. The system further comprises an imaging engine coupled to the imaging core and arranged to provide the imaging core with energy pulses to cause the imaging core to transmit the ultrasonic energy pulses. The energy pulses are arranged in repeated sequences and the energy pulses of each sequence have varying characteristics.

Each sequence of energy pulses may include at least two pulses, as for example, three pulses. The varying characteristic may be pulse energy, frequency, or bandwidth.

The imaging engine may include a processor that processes the reflected ultrasonic energy pulses in image frames and a detector that detects the varying characteristic in the reflected ultrasonic energy pulses. The imaging engine processes the frames according to the detected varying characteristic.

The imaging engine may be arranged to process only reflected ultrasonic energy pulses having a common detected characteristic. The imaging engine may be further arranged to provide a composite image based upon the varying characteristics of the sequences of reflected ultrasonic energy pulses.

The imaging engine may include a processor that processes the reflected ultrasonic energy pulses in separate image frames, each image frame corresponding to each different energy pulse characteristic and the imaging engine may provide display signals for simultaneously displaying the separate image frames.

The invention further provides a method comprising providing a catheter having an elongated body having a distal end and an imaging core arranged to be inserted into the elongated body, the imaging core being arranged to transmit ultrasonic energy pulses and to receive reflected ultrasonic energy pulses. The method further includes the step of providing the imaging core with energy pulses to cause the imaging core to transmit the ultrasonic energy pulses, wherein the energy pulses are arranged in repeated sequences and wherein the energy pulses of each sequence have varying characteristics.

BRIEF DESCRIPTION OF THE DRAWINGS

The invention, together with further features and advantages thereof, may best be understood by making reference to the following descriptions taken in conjunction with the accompanying drawings, in the several figures of which like reference numerals identify identical elements, and wherein:

FIG. 7 is a block diagram of signal processing paths of an IVUS system for co-registered imaging;

FIG. 23 shows a transverse IVUS image of a stented coronary artery acquired using a medium-transmit energy pulse;

FIG. 24 shows a transverse IVUS image of a stented coronary artery acquired using a low-transmit energy pulse;

DETAILED DESCRIPTION OF THE EMBODIMENTS

Figure 1:
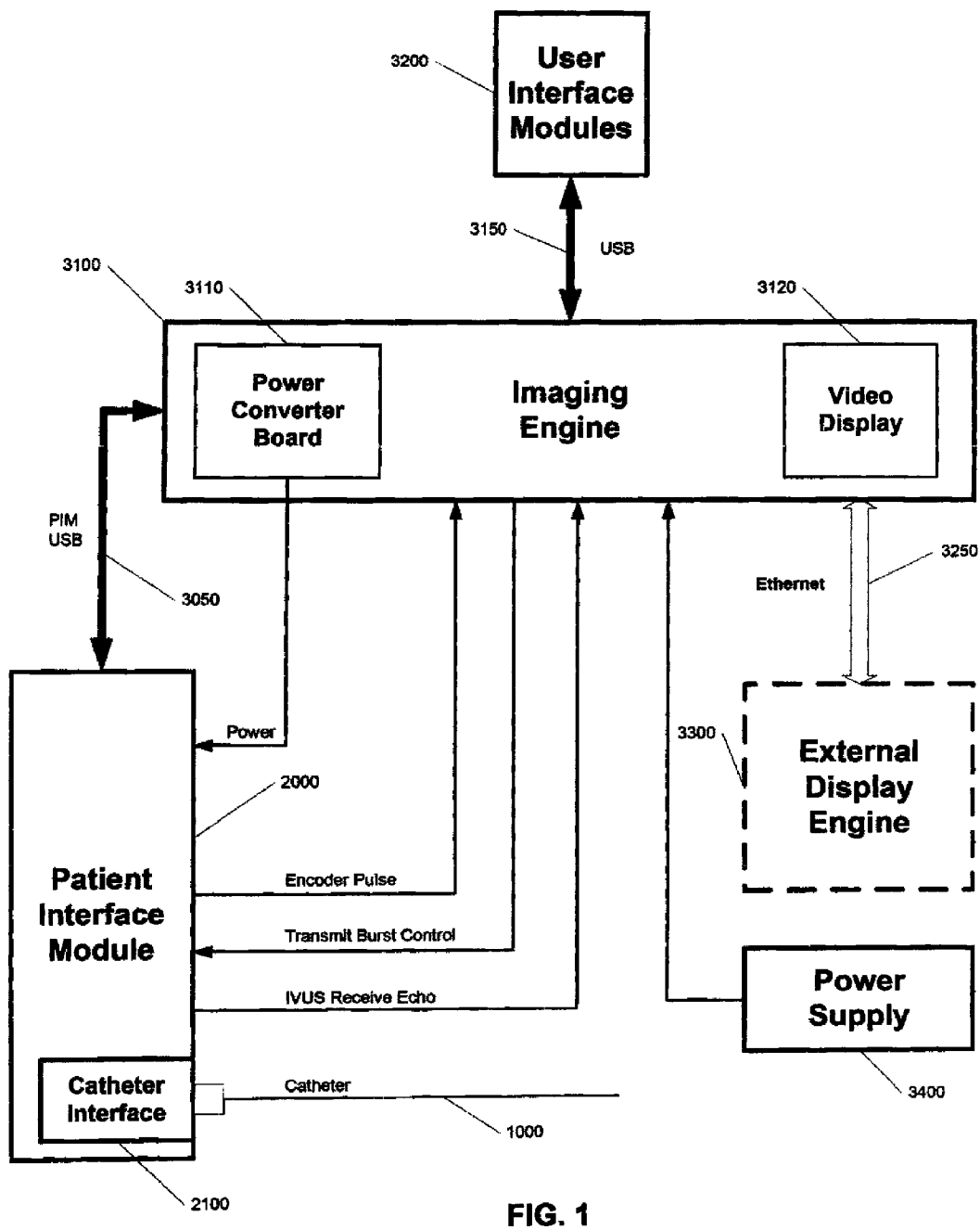
FIG. 1 is a high-level diagram of an IVUS system.

FIG. 1 is a high-level block diagram of an IVUS system comprised of an IVUS imaging catheter 1000, a patient interface module 2000, and an imaging engine 3100. The catheter is typically delivered to a coronary artery via a transfemoral or transradial retrograde route. The imaging catheter 1000 is coupled mechanically and electrically to the patient interface module 2000. The imaging engine 3100 is used to control operation of the patient interface module 2000 and catheter 1000 for purposes of coronary artery imaging. The following descriptions of an IVUS imaging catheter are directed to the case of a mechanically rotating imaging core. Each IVUS image comprises a pre-determined number of vectors (or scan lines) and samples per vector. Most currently available commercial IVUS systems utilize 256 vectors per image. The number of samples per vector varies generally between approximately 256 and 2048 samples for commercially available IVUS systems and depends in part on imaging frequency and data type (e.g., RF or baseband).

Figure 2A:
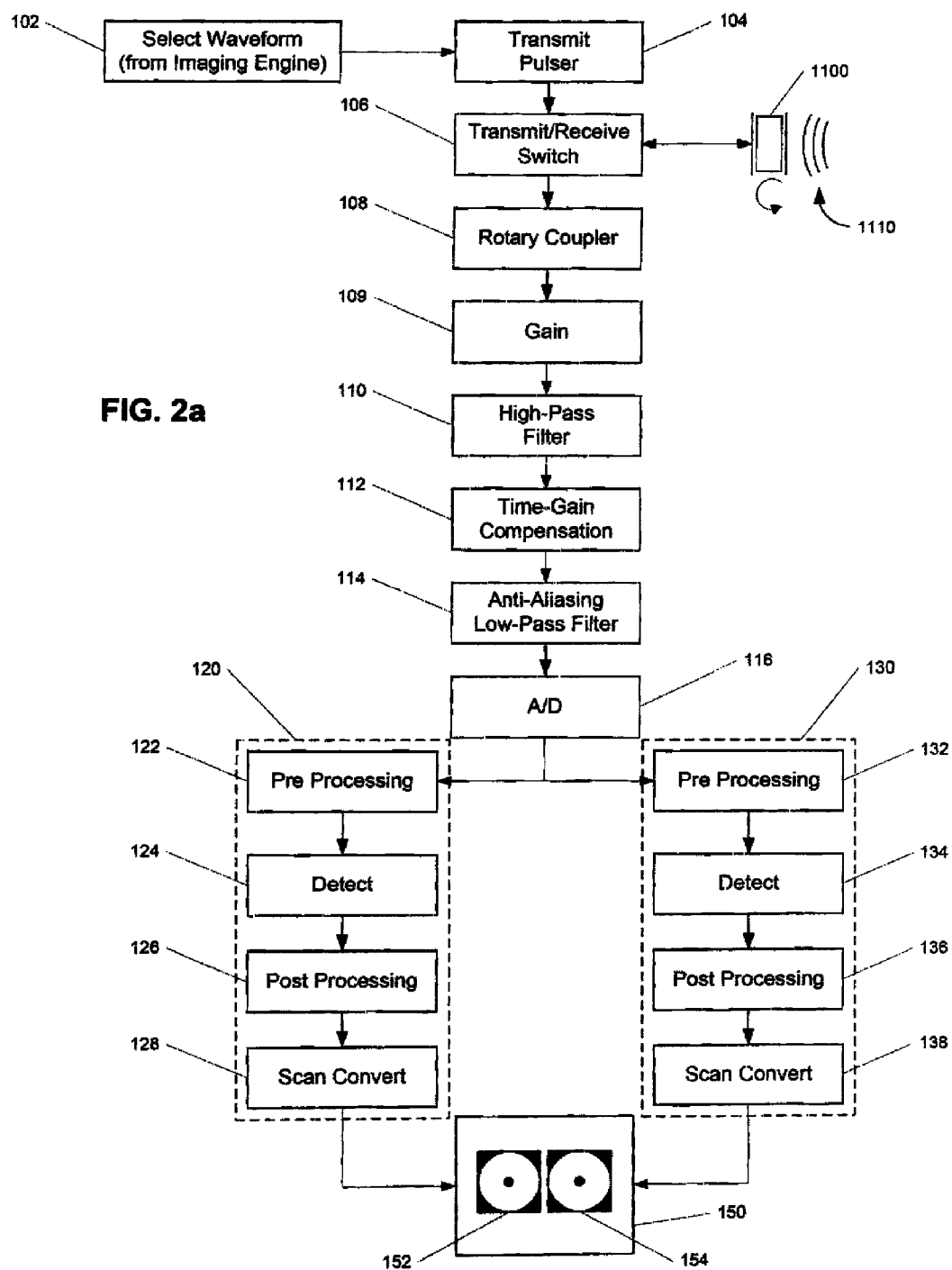
FIG. 2a is a block diagram of signal processing paths of an IVUS system for co-registered imaging.

FIG. 2a is a block diagram of one embodiment of signal processing paths of an IVUS system for co-registered imaging. A waveform is selected in step 102, generally within the imaging engine. A transmit waveform is then generated by a transmit pulser in step 104 that is generally located in the patient interface module. The transmit waveform is sent through a transmit/receive (T/R) switch in step 106 to an ultrasound transducer 1100. The transducer may operate over frequency ranges of 10 MHz to 80 MHz, generally between 20 MHz and 60 MHz for intracoronary imaging.

The transducer emits an ultrasonic pressure field 1110 to insonify the coronary artery. Some ultrasonic energy is backscattered and received by the transducer. The received ultrasound passes through the T/R switch in step 106 and a rotary coupler in step 108. The rotary coupler may be an inductive rotary coupler or a liquid metal rotary coupler. Alternatively, the rotary coupler may be a rotary capacitive coupler as described, for example, in co-pending U.S. patent application Ser. No. 12/465,853 filed May 14, 2009, in the names of Silicon Valley Medical Instruments, Inc. and titled IVUS System with Rotary Capacitive Coupling, which application is hereby incorporated herein by reference in its entirety. The rotary coupler interfaces the mechanically rotating imaging core of the catheter to the non-rotating electronics of the patient interface module.

The received signal then passes through a gain amplifier in step 109, a high-pass filter in step 110, and a time-gain compensation amplifier in step 112. The time-gain compensation is provided, because of the increased attenuation of the ultrasound signal as the signal propagates further into the coronary artery. The signal is next sent through an anti-aliasing low-pass filter in step 114 before digitization in step 116.

The digitized signals are then processed according to multi-frequency techniques comprising a low-frequency path 120 and a high-frequency path 130. The low-frequency and high-frequency processing paths comprise similar processing stages that may differ due to imaging parameters such as pass band, field of view, and signal-to-noise ratio.

Figure 3A:
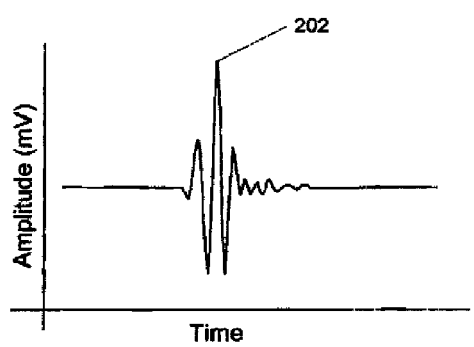
FIGS. 3a and 3b illustrate a time-domain signal and power spectrum, respectively, of short-time pulses.
Figure 3B:
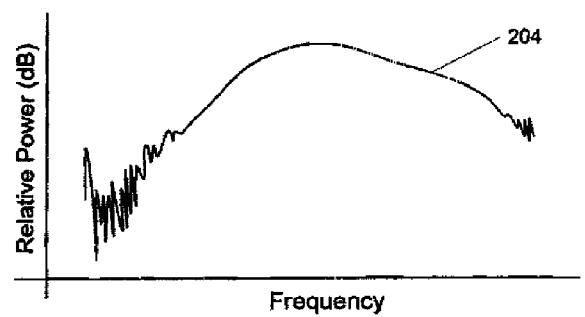
Figure 4A:
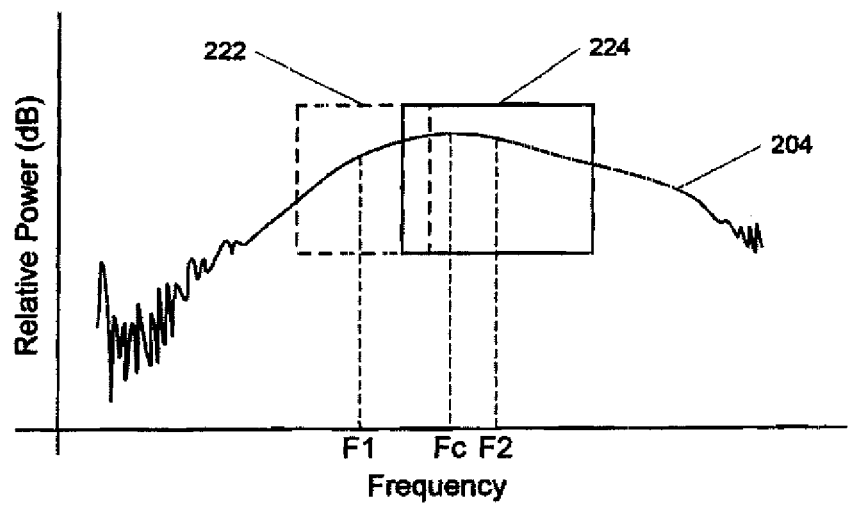
FIG. 4a illustrates a pass band of a broadband power spectrum.
Figure 4B:
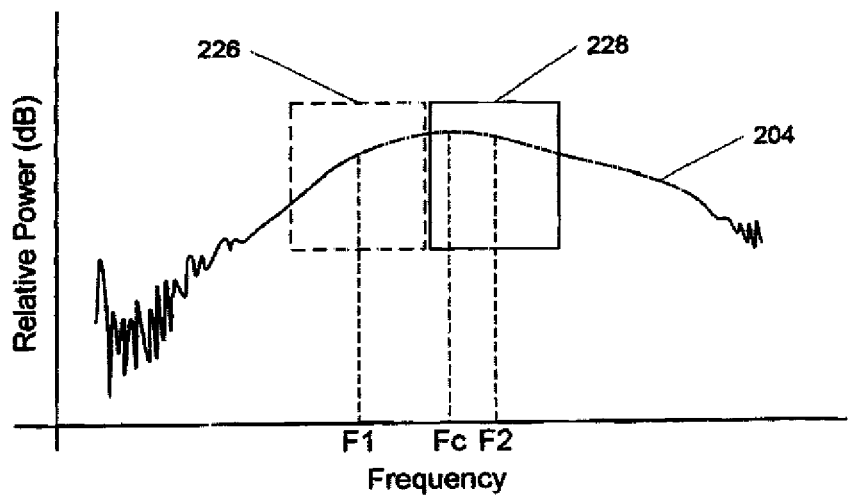
FIG. 4b illustrates another pass band of a broadband power spectrum.

Referring now to FIGS. 3 and 4, the time-domain response 202 and power spectrum 204 are respectively shown in FIGS. 3a and 3b for a short-time pulse of a 60 MHz IVUS imaging transducer having a fractional bandwidth >60%. An important aspect of the present invention is the use of transducers with large fractional bandwidths, generally >50% fractional bandwidth. Transducers having fractional bandwidths <50% may also be used, but the use of such transducers is expected to be less effective with reduced utility. Another important aspect of the present invention is the use of transducers with uniformly high sensitivities across the useful bandwidths. The selected low and high frequencies may comprise overlapping bandwidths 222, 224 or non-overlapping bandwidths 226, 228 with corresponding pass band center frequencies F1, F2 as illustrated respectively in FIGS. 4a and 4b. A potential benefit of the use of overlapping bandwidths is that wider bandwidths generate images having better spatial resolution. In one embodiment of the present invention, the low pass band center frequency F1 is 40 MHz, the high pass band center frequency F2 is 60 MHz, the low pass band 222 is 30 MHz to 50 MHz, and the high pass band 224 is 45 MHz to 75 MHz. In another embodiment of the present invention, the catheter comprises a broadband 40 MHz transducer, the low pass band center frequency is 30 MHz, and the high pass band center frequency is 50 MHz. In still another embodiment of the present invention, the catheter comprises a broadband 35 MHz transducer, the low pass band center frequency is 25 MHz, and the high pass band center frequency is 40 MHz.

Referring again to FIG. 2a, the low-frequency path digitized data are first pre-processed in step 122. Pre-processing, as known in the art, may generally comprise bandpass filtering and vector processing techniques. The envelope of the pre-processed data is detected in step 124 followed by post-processing in step 126. Post-processing generally comprises logarithmic compression and gamma correction to generate a visually appealing and useful image. The post-processed data are then scan converted in step 128 from polar coordinates to Cartesian coordinates. Pre-processing, detection, post-processing, and scan conversion are signal and image processing techniques known to those skilled in the art of medical ultrasound imaging.

The high-frequency path digitized data are processed in an analogous manner. The high-frequency path digitized data are first pre-processed in step 132. Pre-processing, again, generally comprises bandpass filtering and vector processing. The envelope of the pre-processed data is detected in step 134 followed by post-processing in step 136. Post-processing generally comprises logarithmic compression and gamma correction to generate a visually appealing and useful image. The post-processed data are then scan converted in step 138 from polar coordinates to Cartesian coordinates.

The low-frequency and high-frequency scan-converted images 152, 154 are then simultaneously displayed in step 150. A low-frequency image comprises better contrast between blood and non-blood tissues to facilitate lumen border detection. A high-frequency image comprises better spatial resolution of lesion features such as thin fibrous caps. The low-frequency and high-frequency scan-converted images 152,154 are co-registered, because the same ultrasound data are used to generate both images.

Figure 5A:
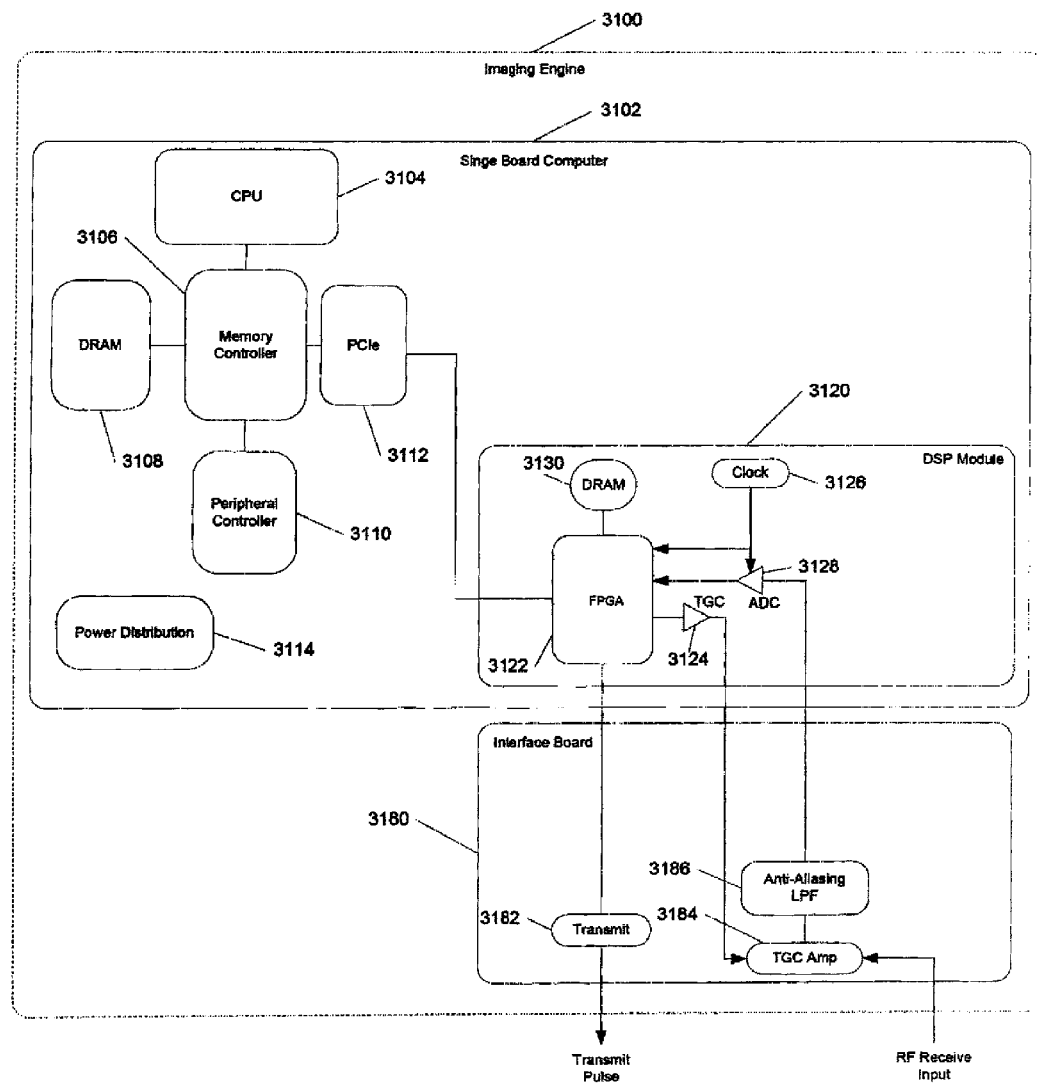
FIG. 5a is a block diagram of an imaging engine.

The signal processing paths illustrated in FIG. 2a can be implemented in numerous physical configurations. An important aspect of the present invention is the physical configuration of the imaging engine. FIG. 5a is a block diagram for one embodiment of the imaging engine 3100 comprising a single board computer 3102, a dedicated digital signal processing (DSP) module 3120, and an interface board 3180. The DSP module 3120 is used to select the transmit waveform 3182 to be sent to the patient interface module. The time-gain compensation amplifier 3184 and anti-aliasing low-pass filter 3186 are located on the interface board 3180. The analog-to-digital converter (or digitizer) 3128 is located in the DSP module 3120. The DSP module 3120 may further comprise a field-programmable gate array (FPGA) 3122. The low-frequency signal and high-frequency signal processing paths 120,130 illustrated in FIG. 2a are generally implemented in the FPGA. An important aspect of this embodiment is that the co-registered imaging is performed by an imaging engine comprising a single analog-to-digital converter and a single FPGA.

Figure 5B:
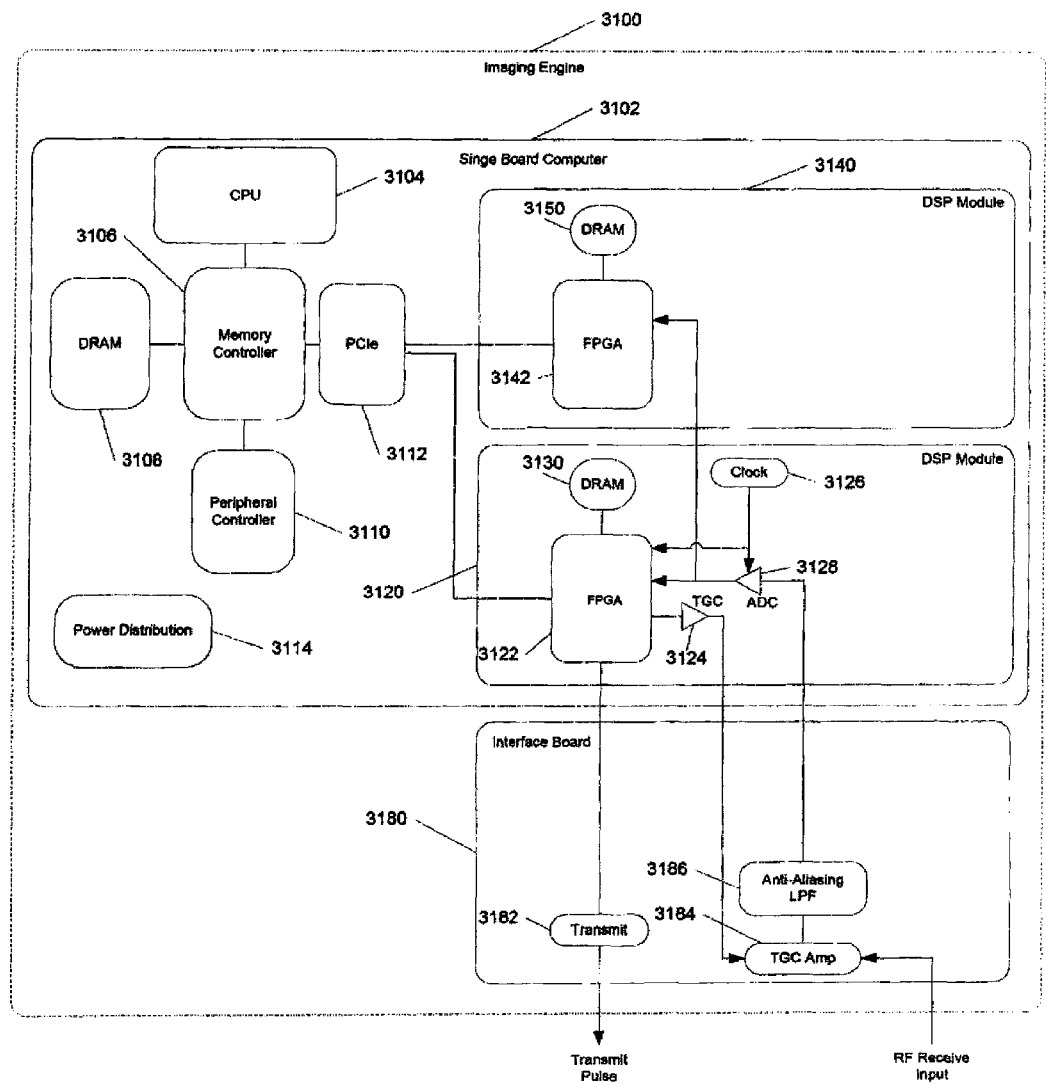
FIG. 5b is another block diagram of an imaging engine.

FIG. 5b is a block diagram of another embodiment of the imaging engine of the present invention comprising a first DSP module 3120 and a second DSP module 3140 wherein a single analog-to-digital converter (or digitizer) 3128 and two FPGAs 3122, 3142 are available. The addition of a second DSP module comprising an FPGA provides increased computational processing power at the expense of increased device complexity and cost. The same digitized data are processed by both FPGAs.

Figure 5C:
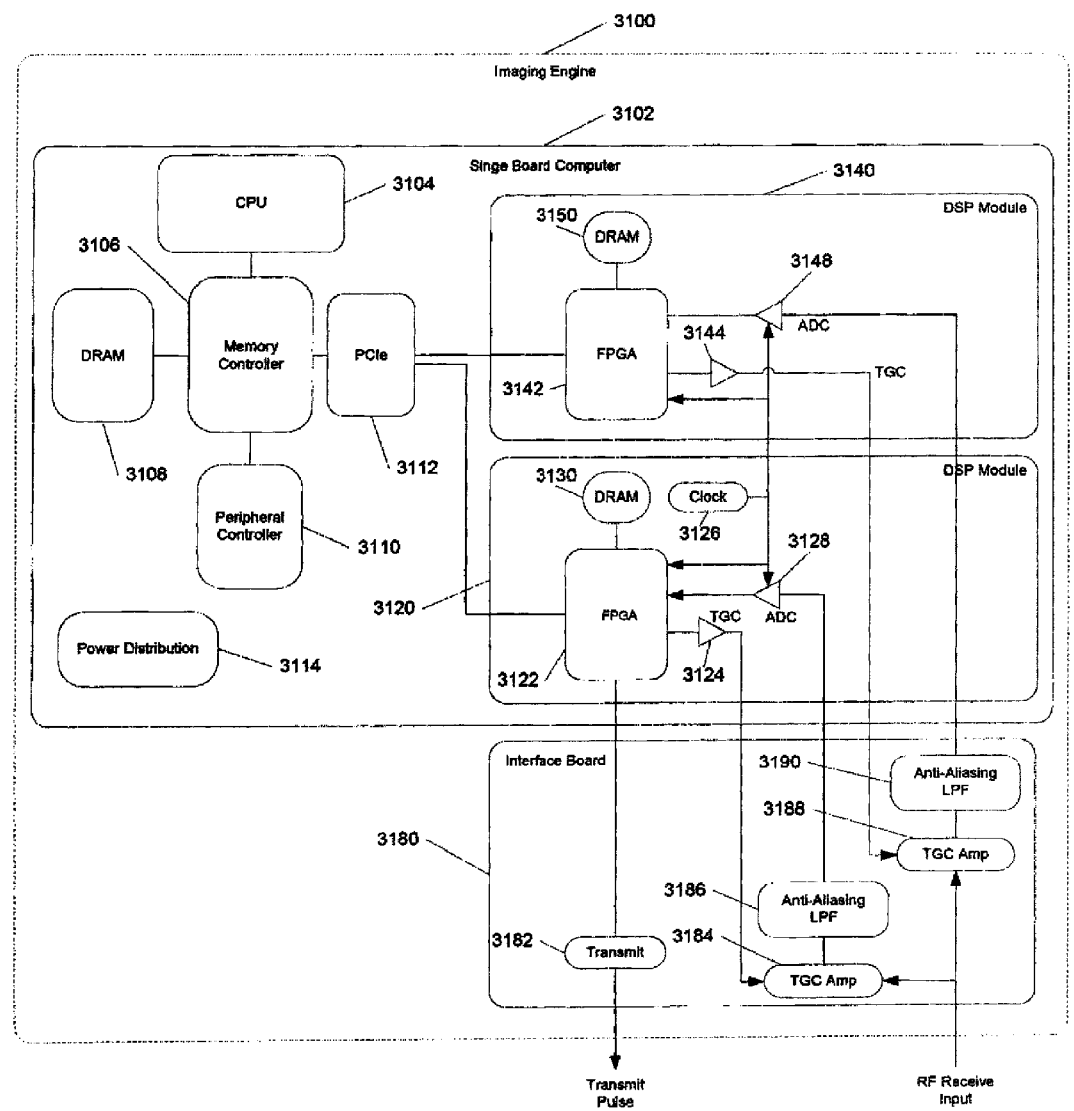
FIG. 5c is still another block diagram of an imaging engine.

FIG. 5c is a block diagram of still another embodiment of the imaging engine of the present invention comprising a first DSP module 3120 and a second DSP module 3140 wherein two analog-to-digital converters (or digitizers) 3128, 3148 and two FPGAs 3122, 3142 are available. A sampling clock 3126 synchronizes both digitizers 3128, 3148. The embodiment of the 2 digitizer/2 FPGA imaging engine further comprises a second time-gain compensation amplifier 3188 and second anti-aliasing low-pass filter 3190. The addition of a second digitizer 3148, time-gain compensation amplifier 3188, low-pass filter 3190 provides increased computational processing power and flexibility at the expense of increased device complexity. The added flexibility enables compensation for differing attenuation of the ultrasound pressure wave through the tissue resulting from the different frequency bands.

Figure 2B:
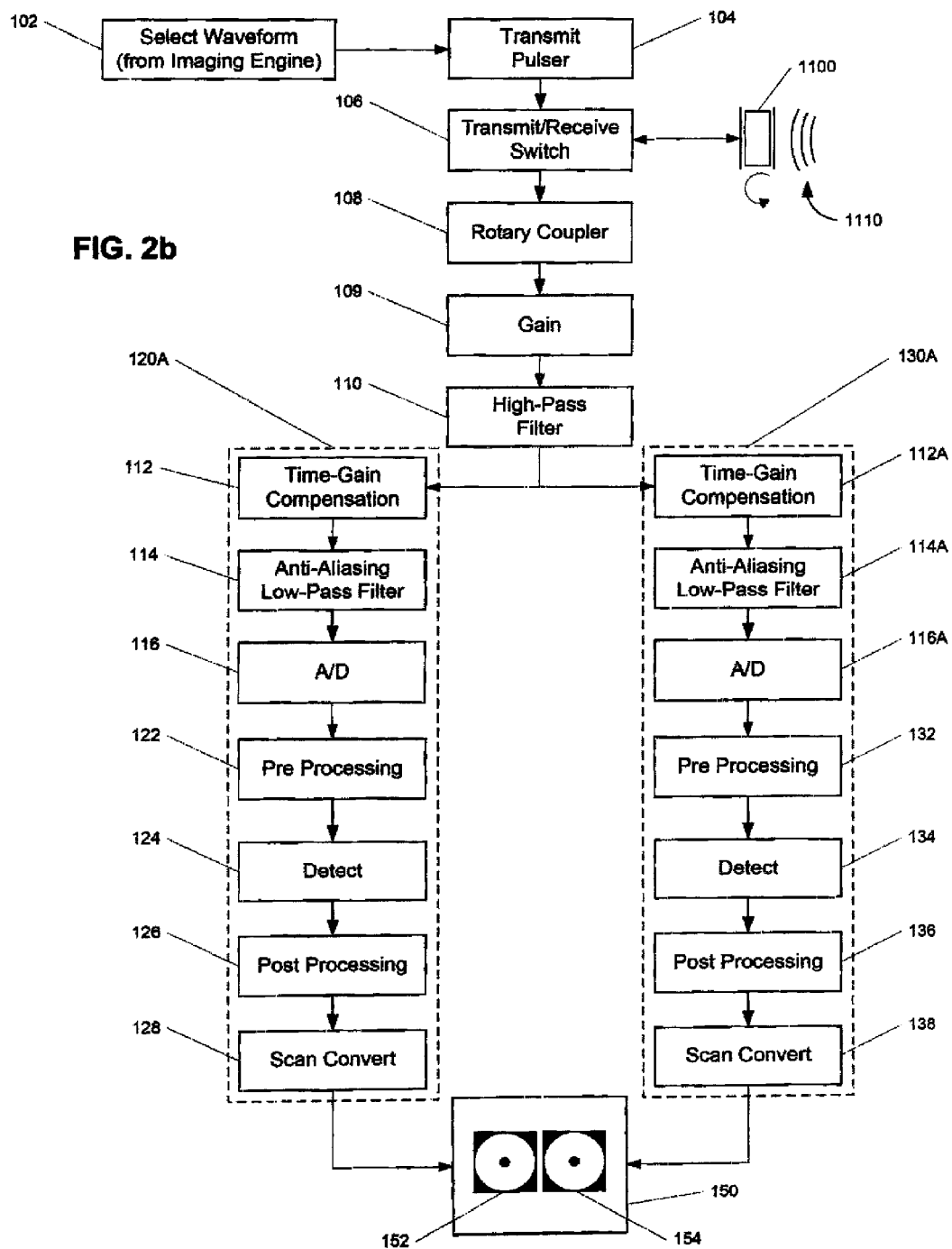
FIG. 2b is another block diagram of signal processing paths of an IVUS system for co-registered imaging.

FIG. 2b is a block diagram of another embodiment of signal processing paths of an IVUS system for co-registered imaging comprising an embodiment of the imaging engine illustrated in FIG. 5c. The signal scattered back from the tissue is received by the transducer 1100 and then passes through a transmit/receive switch in step 106, a rotary coupler in step 108, a gain amplifier in step 109, and a high-pass filter in step 110. The high-pass filtered signals are then processed according to multi-frequency techniques comprising a low-frequency processing path 120A and a high-frequency processing path 130A. The low-frequency processing path 120A and high-frequency processing path 130A include similar processing stages that may differ due to imaging parameters such as pass band, field of view, and signal-to-noise ratio. Time-gain compensation in step 112 is first applied to the low-frequency path signal. Time-gain compensation is provided, because of the increased attenuation of the ultrasound signal as the signal propagates further into the coronary artery. The TGC-amplified low-frequency path signal is next sent through an anti-aliasing low-pass filter in step 114 before analog-to-digital (A/D) conversion (or digitization) in step 116. The low-frequency path digitized data are first pre-processed in step 122. Pre-processing generally comprises bandpass filtering and vector processing techniques. The envelope of the pre-processed data is detected in step 124 followed by post-processing in step 126. Post-processing generally comprises logarithmic compression and gamma correction to generate a visually appealing and useful image. The post-processed data are then scan converted in step 128 from polar coordinates to Cartesian coordinates.

The high-frequency path 130A signals are processed in an analogous manner. Time-gain compensation in step 112A, anti-aliasing low-pass filter in step 114A, and A/D conversion in step 116A occur first after high-pass filtering in step 110. The high-frequency digitized data are then pre-processed in step 132. Pre-processing generally comprises bandpass filtering and vector processing. The envelope of the pre-processed data is detected in step 134 followed by post-processing in step 136. Post-processing generally comprises logarithmic compression and gamma correction to generate a visually appealing and useful image. The post-processed data are then scan converted in step 138 from polar coordinates to Cartesian coordinates. The low-frequency and high-frequency scan-converted images 152, 154 are then simultaneously displayed in step 150. The multi-frequency signal processing paths split after high-pass filtering in step 110 in the embodiment of the signal processing paths shown in FIG. 2b whereas the multi-frequency signal processing paths split after A/D conversion in step 116 in the embodiment of the signal processing paths shown in FIG. 2a. The split of the multi-frequency signal processing paths after high-pass filtering provides for time-gain compensation appropriate for different imaging frequencies.

Figure 6A:
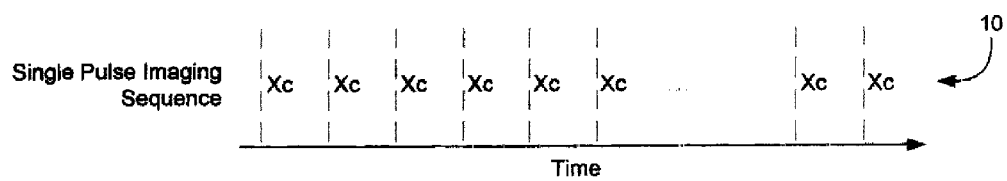
FIGS. 6a-6d illustrate first, second, third, and fourth representative transmit pulse sequences, respectively.
Figure 6B:
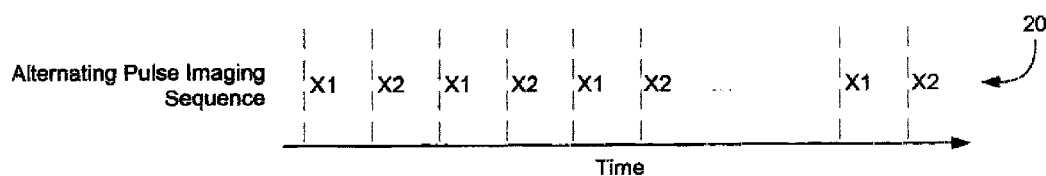
Figure 6C:
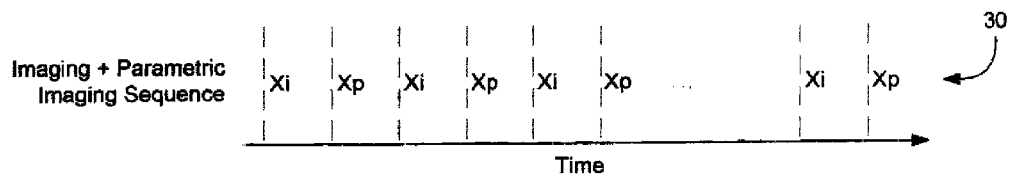
Figure 6D:
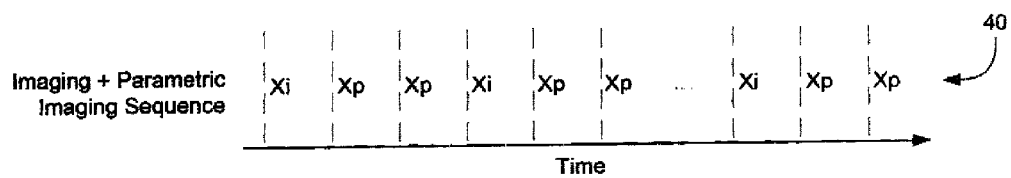

Referring now to FIGS. 6a-6d, a series of imaging waveform sequences are illustrated. FIG. 6a illustrates one embodiment in which a single pulse sequence 10 comprises transmitting the same waveform Xc for each vector of an IVUS image. FIG. 6b illustrates another embodiment comprising a pulse sequence 20 of alternating low-frequency X1 and high-frequency X2 waveforms. A potential advantage of an alternating pulse sequence over a single pulse sequence is that the transmitted energy can be increased or decreased for the selected pass bands of the multi-frequency processing. The ability to adjust transmit energy may benefit image quality of co-registered images that are simultaneously displayed. FIG. 6c illustrates still another embodiment comprising a pulse sequence 30 of alternating imaging Xi and parametric imaging Xp waveforms. The imaging waveform Xi may include a Xc, X1, or X2 waveform. The parametric imaging waveform Xp is selected to optimize analysis of at least one ultrasound tissue classification parameter including integrated backscatter, attenuation, strain, and motion. The use of a more narrowband waveform may provide benefit to correlation-based or Doppler-based motion analysis. FIG. 6d illustrates still yet another embodiment including a pulse sequence 40 of alternating imaging and parametric imaging waveforms Xi, Xp wherein multiple parametric imaging waveforms Xp are transmitted between imaging waveforms Xi. The use of repeated pulses may provide additional benefits for signal-to-noise conditions.

Thus, as may be seen from the above, and in accordance with aspects of the present invention, an imaging engine coupled to an imaging core may be arranged to provide the imaging core with energy pulses to cause the imaging core to transmit ultrasonic energy pulses. The energy pulses may be arranged in repeated sequences and the energy pulses of each sequence may have varying characteristics. For example, each sequence of energy pulses may include at least two pulses. Also, the varying characteristic may be pulse energy.

FIG. 7 shows a block diagram of one embodiment of signal processing paths of an IVUS system for co-registered imaging wherein the co-registered images include a grayscale image 182 and a parametric image 184. The parametric image 184 may include a multi-parametric image. The transmit waveform selected in step 102 and sent from the imaging engine may include a single pulse sequence 10 or an imaging and parametric imaging pulse sequence 30 as illustrated in FIGS. 6a and 6c. The signal processing path to the digitization step 116 is similar to the signal processing path for the multi-frequency imaging illustrated in FIG. 2a.

The digitized signals are then processed according to a grayscale imaging path 160 and a parametric imaging path 170. The grayscale imaging path digitized data are first pre-processed in step 162. Pre-processing generally comprises bandpass filtering and vector processing techniques. The envelope of the pre-processed data is detected in step 164 followed by post-processing in step 166. Post-processing generally comprises logarithmic compression and gamma correction to generate a visually appealing and useful image. The post-processed data are then scan converted in step 168 from polar coordinates to Cartesian coordinates.

The processing stages of the parametric imaging path 170 include a pre-processing step 172, a parametric analysis step 174, a post-processing step 176, and a scan conversion step 178. The particular details of each parametric imaging processing step depend upon the at least one parameter to be calculated.

In one embodiment of the present invention a parametric image of integrated backscatter is generated. The integrated backscatter pre-processing step 172 comprises bandpass filtering and vector processing techniques. The filter pass band may be determined from the −3 dB bandwidth of the transducer. The integrated backscatter parametric analysis in step 174 may include a sliding window technique. Sliding window techniques are known to those skilled in the art of ultrasound tissue characterization.

Figure 8:
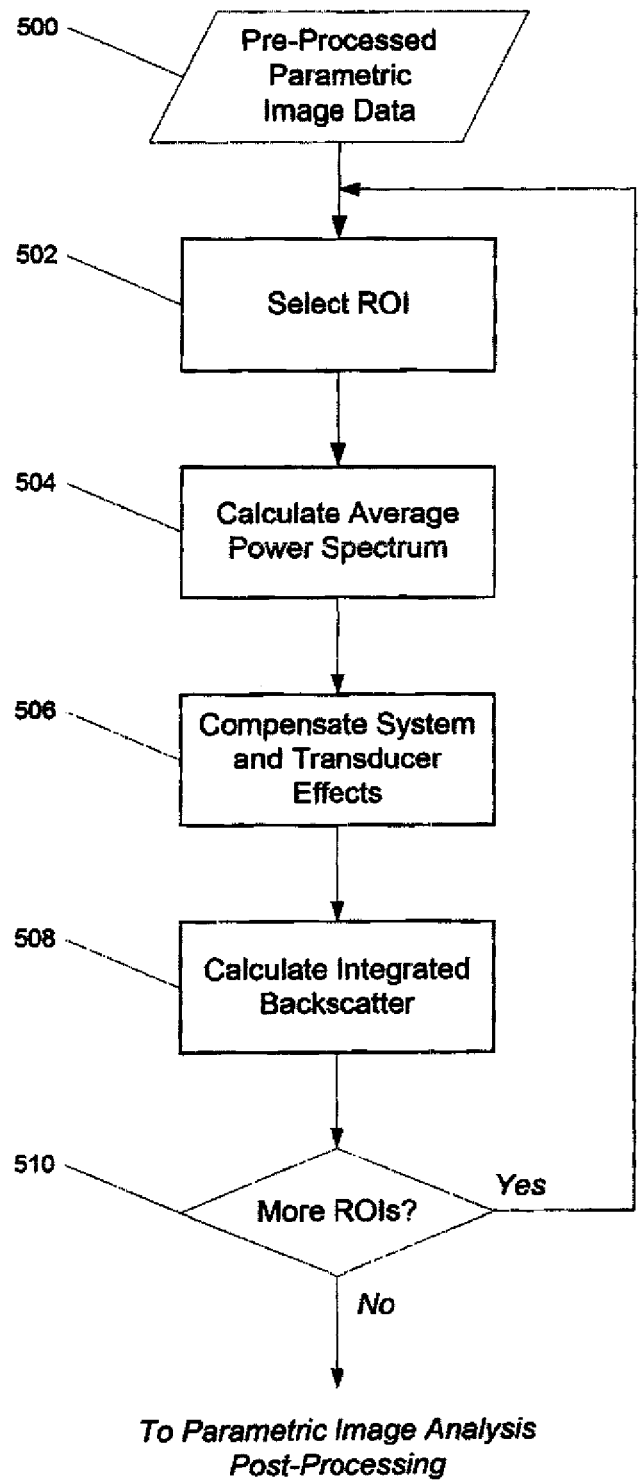
FIG. 8 is a block diagram of signal processing steps for calculation of an integrated backscatter parameter.

Referring now to FIG. 8, a block diagram illustrates one embodiment of the signal processing stages for calculation of the integrated backscatter parameter using a sliding window technique. A region of interest (ROI) of the pre-processed data 500 is first selected in step 502. A time-domain window such as a Hamming or Hann window may be applied to each vector of the ROI to minimize edge discontinuities in Fast Fourier Transform (FFT) spectral analysis at the cost of reduced frequency resolution. The ROI comprises a pre-determined number of vectors and vector samples. The number of vectors and vector samples depends upon details including vector density, sample rate, optimal ROI size, and signal-to-noise metrics.

In one embodiment of the present invention the system provides a vector density of 1024 vectors per IVUS image and a sample rate of $400 \times 10^6$ samples/s. An optimal ROI size balances a minimal radial extent of the ROI with a maximal signal-to-noise ratio. A lateral extent of the ROI comparable to the radial extent can facilitate subsequent parametric image analysis. Multiple vectors also permit signal averaging. Further, the selected ROI size may be range dependent, because the physical vector spacing increases with range. An ROI size of 7 vectors and 32 samples at a range of 1.5 mm provides a ROI that is approximately 60 μm×60 μm. This size may be suitable for small-scale atherosclerotic lesion features such as thin-fibrous caps.

The average power spectrum is calculated in step 504 for the ROI by calculating the power spectrum of each vector and then averaging. The power spectrum is calculated generally using FFT techniques. Averaging is performed generally in the logarithmic (dB) domain, but may be performed in the linear domain. The average power spectrum may then be compensated for system and transducer effects in step 506 comprising range-dependent sensitivity and frequency-dependent transducer sensitivity. The integrated backscatter parameter is calculated in step 508 by summing the compensated, average power spectrum values of the selected bandwidth and dividing by said selected bandwidth. Additional ROIs are selected by sliding the window (or ROI) over the pre-processed data 500 or pre-defined subset of the pre-processed data. The degree of overlap of ROIs is selected to balance smoothing in the parametric image by maximizing overlap with computational cost by minimizing overlap. For a ROI size of 7 vectors×32 samples, the sliding window overlap generally comprises between 16 samples (or 50%) and 24 samples (or 75%) along a vector and between 4 vectors (or approximately 50%) and 6 vectors (or approximately 85%) across vectors. The integrated backscatter parametric data are sent to the post-processing step 176 (of FIG. 7) when there are no more ROIs remaining to be analyzed.

Post-processing in step 176 of the integrated backscatter image includes thresholding and gamma correction. In one embodiment of the present invention, the integrated backscatter image is thresholded to display lipid-rich ROIs which are known to have relatively low integrated backscatter values. In alternative embodiments, the integrated backscatter image is thresholded at multiple levels to distinguish multiple tissue types. The post-processed integrated backscatter image is then scan converted in step 178.

The scan-converted grayscale image and scan-converted integrated backscatter parametric image are then simultaneously displayed in step 180. A grayscale image may provide better structural detail. An integrated backscatter parametric image may provide better plaque composition detail. Further, the grayscale and integrated backscatter parametric images 182,184 are co-registered, because the same ultrasound data are used to generate both images.

Figure 9:
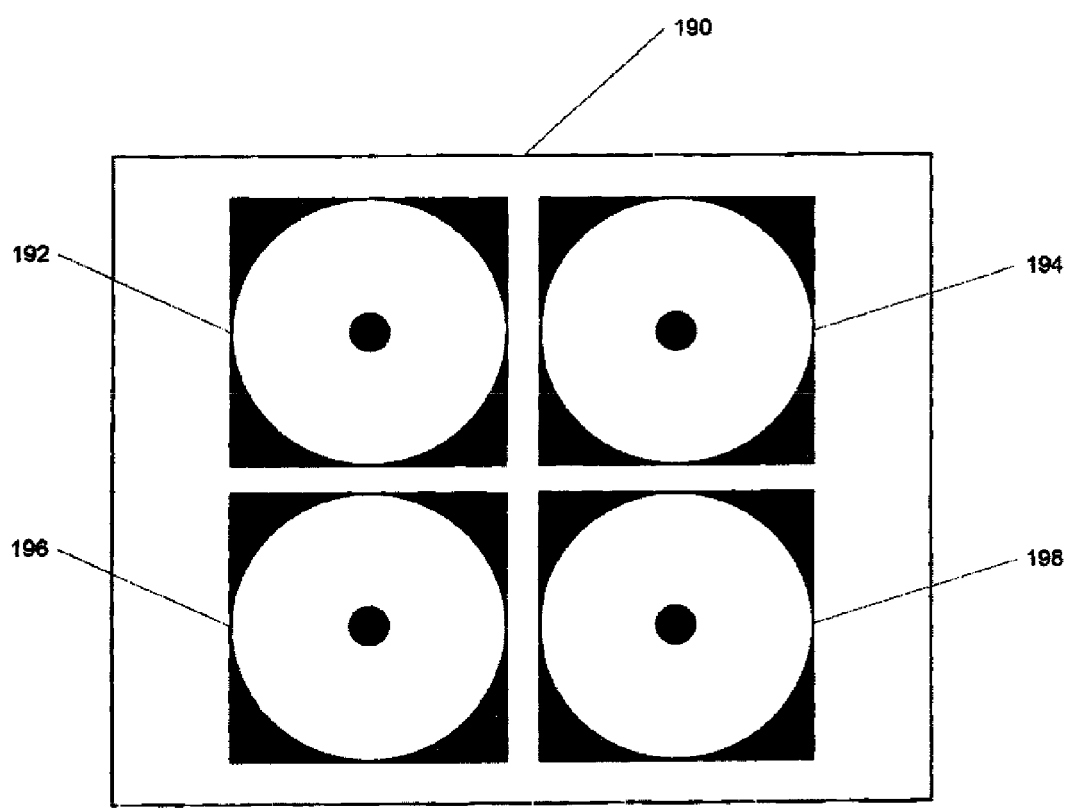
FIG. 9 illustrates a display comprising multiple co-registered images.

FIG. 9 illustrates a display 190 comprising four co-registered images 192, 194, 196, 198. The four co-registered images may comprise at least one grayscale image and at least one parametric image. In one embodiment of the present invention, the display comprises a 40 MHz grayscale image, a 60 MHz grayscale image, and an integrated backscatter parametric image.

Figure 10A:
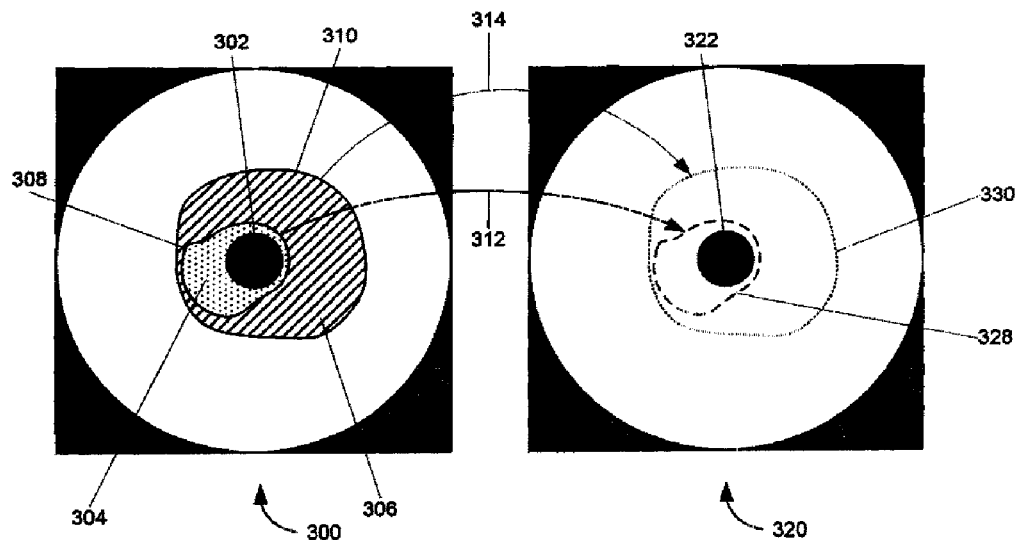
FIGS. 10a and 10b illustrate feature mapping between co-registered images.

The present invention facilitates mapping of image features between co-registered images. IVUS images of lower ultrasound frequencies generally provide better contrast between blood and non-blood tissues whereas IVUS images of higher ultrasound frequencies generally provide better spatial resolution of atherosclerotic lesions. FIG. 10*a* illustrates a first IVUS image 300 of lower frequency and second IVUS image 320 of higher frequency. Catheter masks 302, 322 represent catheter position relative to a coronary artery section. A lumen contour 308 identified in the first image 300 can be mapped 312 to a lumen contour 328 in the second image 320. The lumen contour segments blood 304 from non-blood tissues. A vessel contour 310 identified in the first image 300 can be mapped 314 to a vessel contour 330 in the second image 320. The lumen and vessel contours 308, 310 segment atherosclerotic plaque 306 from other tissues. The mapped contours 328, 330 of the higher-frequency IVUS image enable further processing of the atherosclerotic plaque.

Figure 10B:
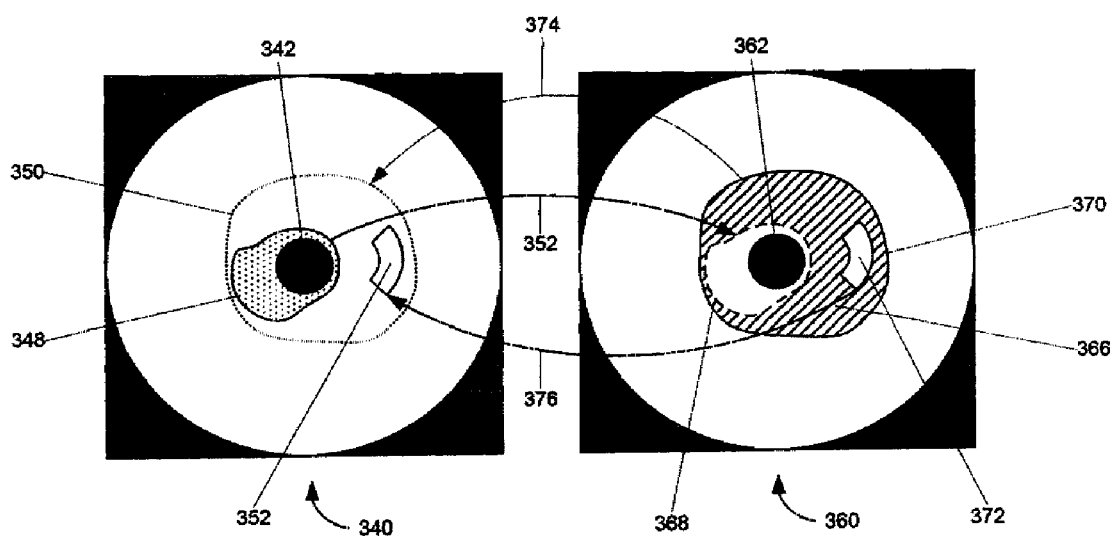

FIG. 10*b* illustrates mapping features more prominent in a first image 340 to a second image 360 and mapping features more prominent in said second image 360 to said first image 340. The first image may comprise a grayscale image, and the second image may comprise a parametric image. A lumen contour 348 in the first image 340 is mapped 352 to a lumen contour 368 in the second image 360. A vessel contour 370 and ROI 372 in the second image 360 are respectively mapped 374, 376 to a second vessel contour 350 and second ROI 352 in the first image 340.

Figure 11:
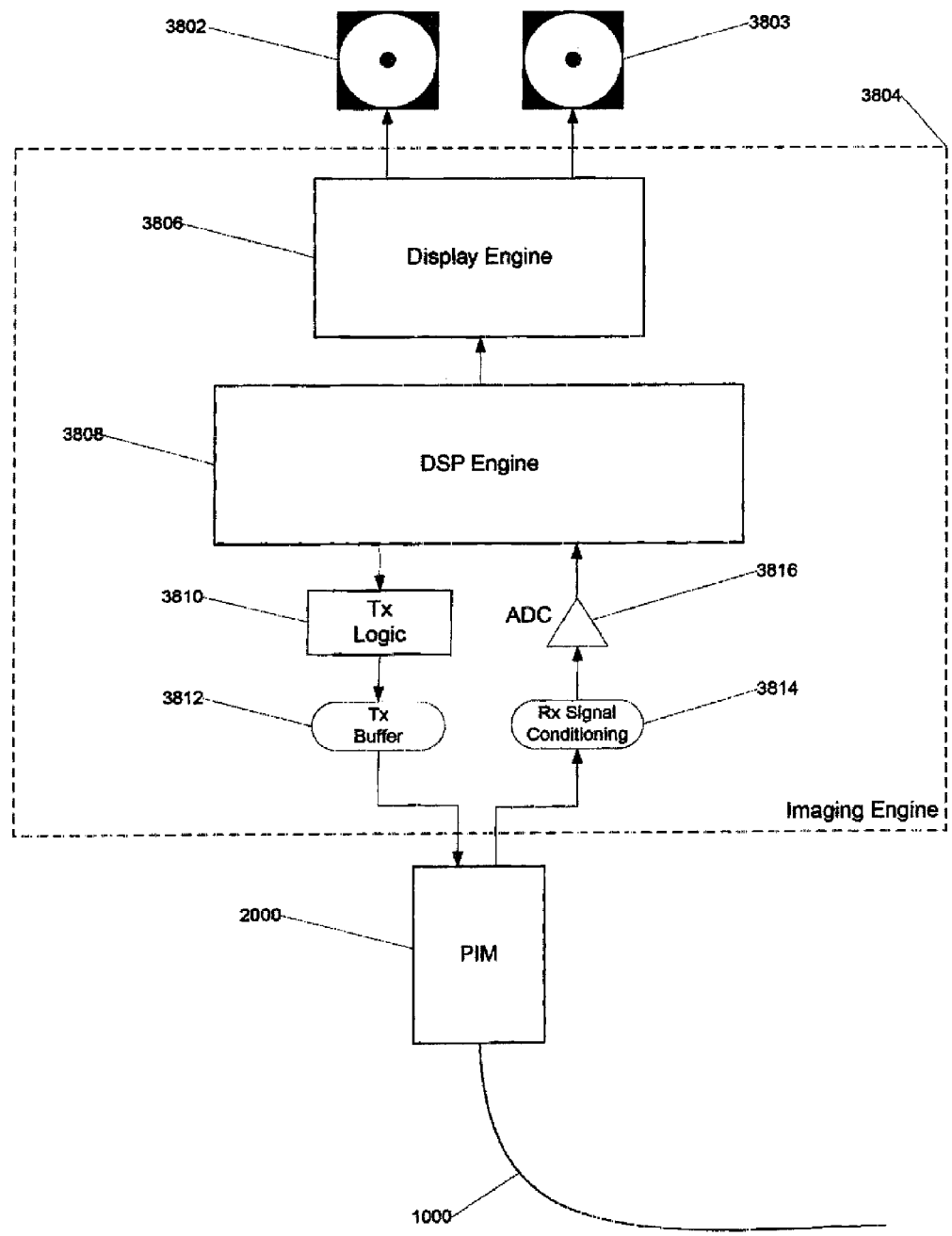
FIG. 11 is a high-level diagram of an IVUS system.

It is desirable that the present invention provide optimal imaging performance and computational efficiency with minimal device complexity. FIG. 11 shows a high-level diagram of one embodiment of an IVUS system for co-registered imaging. The following descriptions of an IVUS system for co-registered imaging are directed to the case of an IVUS system for display of two co-registered grayscale images. The IVUS system comprises two images 3802, 3803, an imaging engine 3804, a patient interface module (PIM) 2000, and an IVUS imaging catheter 1000. The following descriptions of the IVUS imaging catheter 1000 are directed at the case of a mechanically rotating imaging core. The imaging engine 3804 comprises a display engine 3806, a DSP engine 3808, transmit (Tx) logic 3810, a transmit buffer 3812, a receive (Rx) signal conditioning stage 3814, and an analog-to-digital converter (ADC) 3816.

The DSP engine 3808 provides computing power for real-time, simultaneous co-registered imaging. The DSP engine 3808 sends control signals to the transmit logic 3810 that generates an analog transmit pulse sequence. The transmit pulse passes through the transmit buffer 3812 before going to the PIM 2000. The PIM 2000 is the interface between the catheter 1000 and the imaging engine 3804. The PIM 2000 provides for transmitting transducer excitation energy, receiving transducer signal returns, and sending signal returns to the imaging engine 3804. The return signals pass through a receive signal conditioning stage 3814 and analog-to-digital converter 3816. The digitized return signals are then processed in the DSP engine 3808. Image data are sent to the display engine 3806 and streamed for real-time simultaneous display of co-registered images 3802, 3803.

Figure 12:
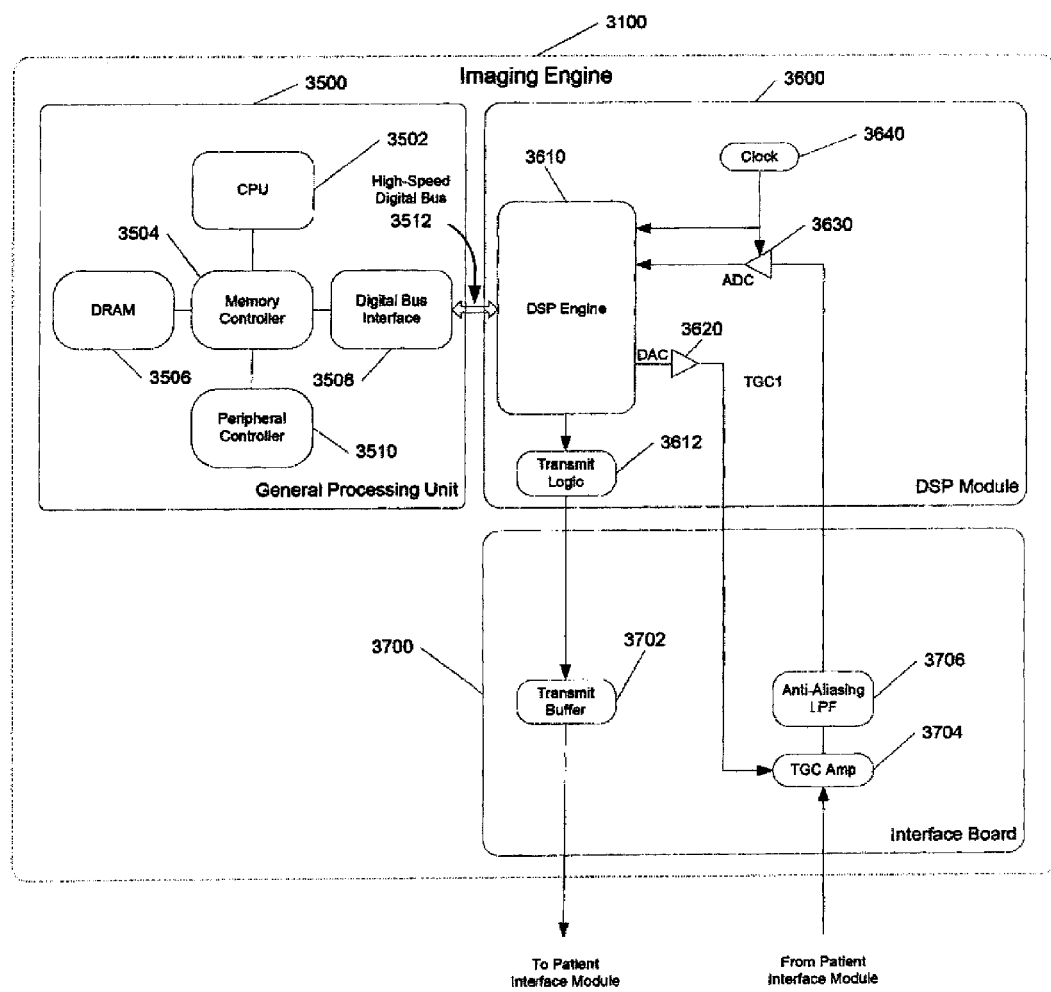
FIG. 12 is a block diagram of a further imaging engine.

FIG. 12 illustrates one embodiment of a physical configuration of the imaging engine 3100. The imaging engine 3100 performs all image generation, display, and control of the entire system. The imaging engine 3100 may include a general processing unit 3500, a DSP module 3600, and an interface board 3700.

The general processing unit 3500 may include a central processing unit (CPU) 3502, a memory controller 3504, dynamic random access memory (DRAM) 3506, a digital bus interface 3508, and a peripheral controller 3510. The DSP module 3600 may include a DSP engine 3610, transmit logic circuitry 3612, a digital-to-analog converter (DAC) 3620, an analog-to-digital converter (ADC) 3630, and a sampling clock 3640. A high-speed digital bus 3512 connects the digital bus interface 3508 to the DSP engine 3610. The interface board 3700 may include a transmit buffer 3702, a time gain compensation (TGC) amplifier 3704, and an anti-aliasing low-pass filter (LPF) 3706.

The DSP engine 3610 controls the transmit logic circuitry 3612 to send an analog transmit signal to the transmit buffer 3702. The analog transmit signal may include a pulse wherein the pulse may include at least one rectangular pulse. The analog transmit signal is sent from the interface board 3700 to the PIM. The DSP engine 3610 further generates a digital TGC signal that is converted by the DAC 3620 to an analog TGC signal. The analog TGC signal provides the level of TGC amplification 3704 applied to signals received from the PIM. The low-pass filter 3706 minimizes aliasing in the TGC-amplified signals.

The anti-aliased TGC-amplified return signals are digitized and then processed by the DSP engine 3610 for co-registered imaging. A sampling clock 3640 synchronizes the ADC (or digitizer) 3630 and DSP engine 3610. Co-registered images are streamed from the DSP engine 3610 to the general processing unit 3500 for display of images.

Figure 13:
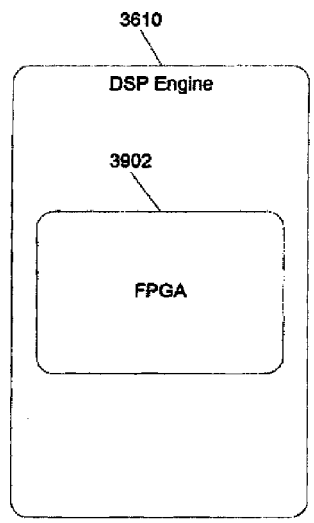
FIGS. 13-17 are block diagrams of digital signal processing engines.
Figure 14:
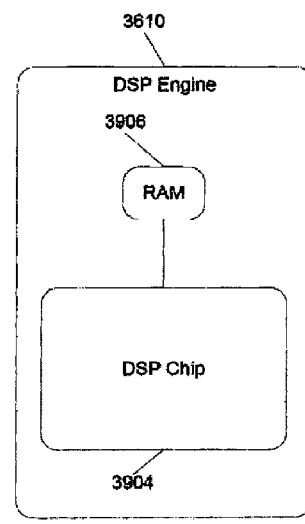
Figure 15:
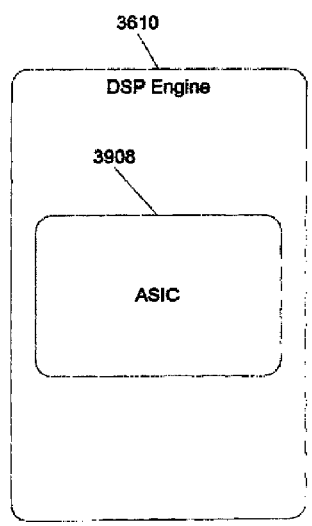
Figure 16:
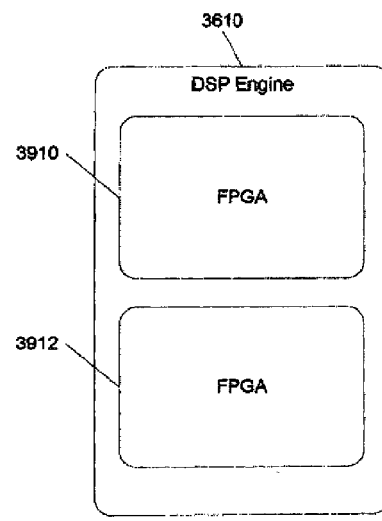
Figure 17:
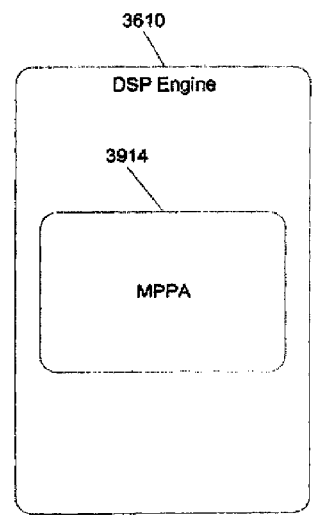

Referring now to FIGS. 13-17, the DSP engine 3610 may include different forms of signal processors. FIGS. 13-15 show diagrams of a DSP engine 3610 including a field-programmable gate array (FPGA) 3902, a DSP chip 3904 and random-access memory (RAM) 3906, or an application-specific integrated circuit (ASIC) 3908. The DSP engine may further include multiple signal processors. FIG. 16 shows a diagram of a DSP engine 3610 that includes a first FPGA 3910 and a second FPGA 3912. FIG. 17 shows a diagram of a DSP engine 3610 that includes a massively parallel processor array (MPPA) 3914 of CPUs and RAM modules. The most cost effective and computationally efficient signal processor will depend on the specific application. Field-programmable gate arrays are commonly used in IVUS imaging systems.

Figure 18:
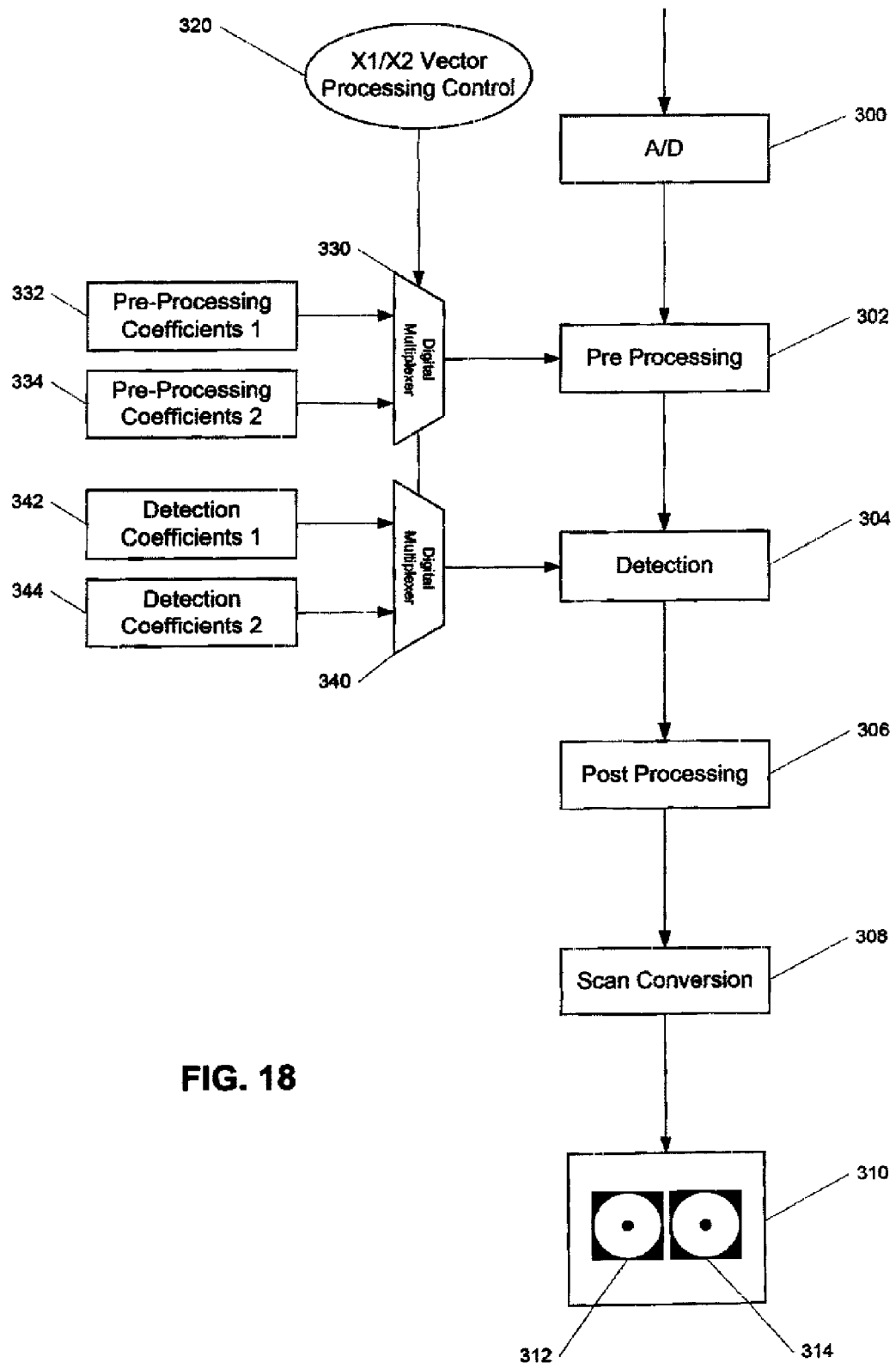
FIG. 18 is a block diagram of the signal processing path of an IVUS system for co-registered imaging.

FIG. 18 illustrates a signal processing path for co-registered multi-frequency imaging that provides for optimizing co-registered grayscale imaging performance while minimizing device cost and complexity. The following descriptions are directed at the case of an alternating transmit pulse sequence 20 as illustrated in FIG. 6b wherein a first pulse sequence X1 has a lower imaging frequency and a second pulse sequence X2 has a higher imaging frequency. A potential advantage of the alternating pulse sequence 20 over a single pulse sequence 10 shown in FIG. 6a is that the transmitted energy can be increased or decreased for the selected pass bands of the multi-frequency processing. The ability to adjust transmit energy may benefit image quality of co-registered images that are simultaneously displayed.

The received signal is converted from analog to digital (A/D) in step 300. The digitized signals are pre-processed in step 302 wherein pre-processing generally includes bandpass filtering and vector processing techniques. The specific form of pre-processing depends on whether the transmit signal is an X1 pulse or X2 pulse. A digital multiplexer 330 receives a first set of pre-processing coefficients 332 and a second set of pre-processing coefficients 334. The pre-processing coefficients include filter coefficients for bandpass filtering. A vector processing control 320 determines which set of pre-processing coefficients to use for pre-processing. The envelope of the pre-processed signal is detected in step 304. The vector processing control 320 determines whether a digital multiplexer 340 selects a first set of detection coefficients 342 or a second set of detection coefficients 344 for detection processing. The detected signal is then post-processed in step 306 wherein post-processing generally comprises logarithmic compression and gamma correction to generate a visually appealing and useful image. The post-processed signals are then scan converted in step 308 from polar coordinates to Cartesian coordinates.

The low-frequency and high-frequency scan-converted images 312, 314 are then simultaneously displayed in step 310. A low-frequency image may provide better contrast between blood and non-blood tissues to facilitate lumen border detection. A high-frequency image may provide better spatial resolution of lesion features. The low-frequency and high-frequency scan-converted images 312, 314 are co-registered, because both sets of image data are acquired at substantially the same time when using alternating transmit pulse sequences.

In another embodiment, the alternating transmit pulse sequence may include alternating groups of pulses. A pulse sequence may include alternating groups of X1 and X2 pulse sequences wherein each group of X1 and X2 pulses includes at least two (2) pulses. The temporal delay will be larger between acquisitions of the X1 and X2 images, but there may be advantages to fewer alternations between X1 and X2 pulse sequences.

A key advantage of the signal processing path illustrated in FIG. 18 is that only one digitizer is required. Further, the digital signal processing can be performed in a single FPGA. Still further, the multi-frequency processing can be performed without duplication of signal processing stages.

An important aspect of the present invention is the use of an IVUS system for co-registered imaging comprising an imaging engine, a patient interface module, and an IVUS catheter. The imaging engine may comprise a general processing unit, a DSP module, and an interface board. The DSP module comprises an analog-to-digital converter and a DSP engine. The DSP engine may comprise a FPGA, DSP chip, or ASIC. The DSP engine may alternatively comprise multiple FPGAs or a massively parallel processing array of CPUs and RAM modules. Another important aspect of the present invention is the use of an IVUS catheter comprising a broadband (>50% fractional bandwidth) ultrasound transducer with high sensitivity wherein both a low pass band and a high pass band can be used to generate grayscale images. Low pass band and high pass band center frequencies may respectively comprise 40 MHz and 60 MHz, 30 MHz and 50 MHz, 25 MHz and 40 MHz, and other combinations with different frequency spacing. Still another important aspect of the present invention is the use of a programmable transmit pulse sequence. The transmit pulse sequence may comprise a single pulse imaging sequence, an alternating low-frequency and high-frequency imaging sequence, or an alternating imaging and parametric imaging sequence. Still yet another important aspect of the present invention is the display of at least two (2) co-registered images comprising at least one grayscale image. The co-registered images may further comprise at least one parametric image. A further important aspect of the present invention is the mapping of image features between co-registered images wherein image features comprise contours and regions of interest.

Figure 19:
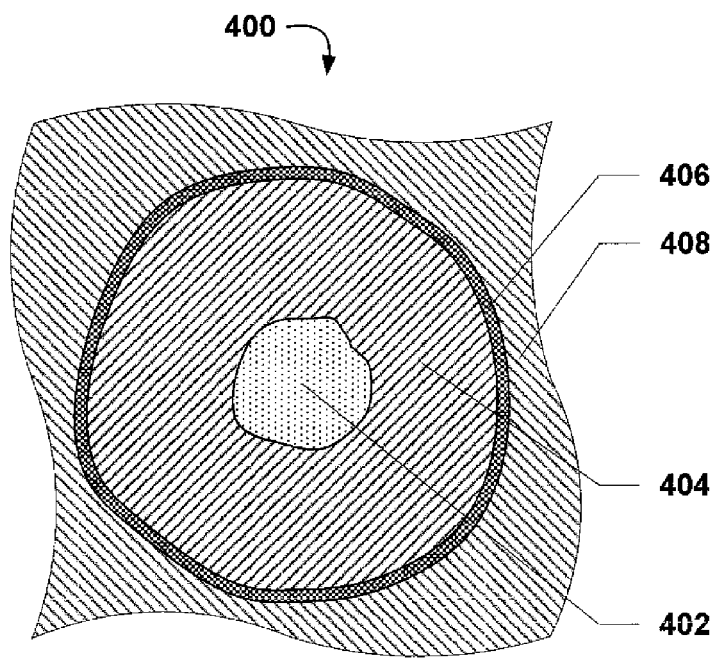
FIG. 19 is a cross-sectional view of a stenosed coronary artery.
Figure 20:
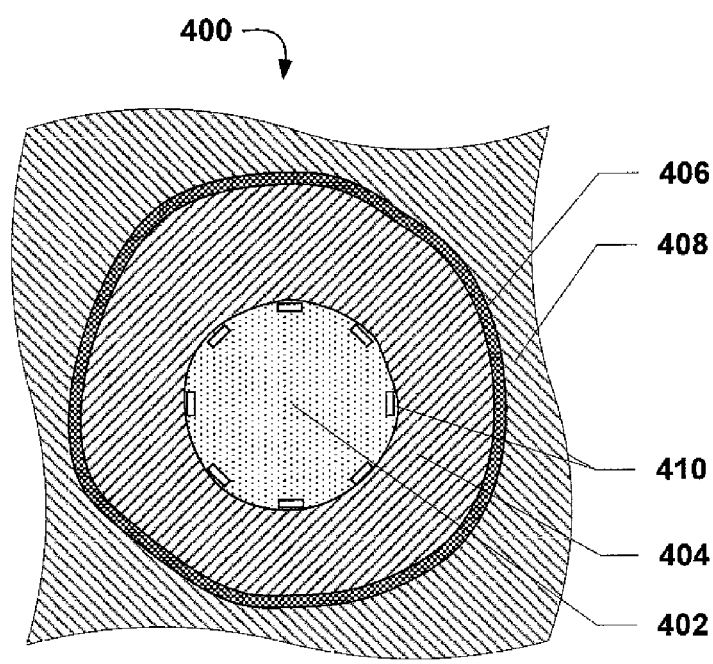
FIG. 20 is a cross-sectional view of a coronary artery with an implanted stent.

It is also desirable to provide improved contrast resolution for imaging of coronary arteries having implanted stents. The ability to detect and measure stent healing, or early neotissue growth over coronary stent struts, is of particular relevance. FIG. 19 shows an illustration of a cross-section of a stenosed coronary artery 400. The coronary artery includes a blood-filled lumen 402, an intimal plaque layer 404, a medial layer 406, and an adventitial layer 408. The lumen generally has a cross-sectional area less than 4 mm$^2$. FIG. 20 shows an illustration of the same coronary artery 400 as in FIG. 19 after stent implantation. The stent struts 410 are positioned in proximity to the lumen-plaque border. The stent provides for an increased lumen cross-sectional area to enable improved blood flow through the artery.

Figure 21:
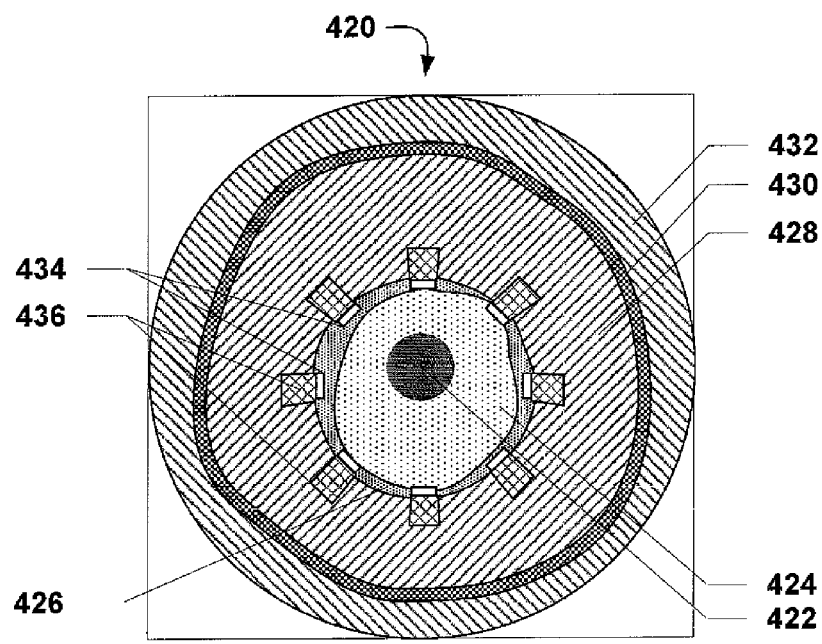
FIG. 21 shows a transverse IVUS image of a stented coronary artery acquired using a high-transmit energy pulse.

FIG. 21 shows a transverse IVUS image 420 of a stented coronary artery acquired with a high-transmit energy pulse having an amplitude generally greater than 50 V. The transverse IVUS image 420 includes a catheter mask 422 to indicate position of the IVUS catheter relative to the coronary artery. The IVUS image 420 further shows ultrasound reflections from a blood-filled lumen 424, neotissue growth 426, an intimal plaque layer 428, a medial layer 430, and an adventitial layer 432. The neotissue growth 426 is a result of the stent healing process. Uncovered struts of drug-eluting stents are considered a factor in the adverse event of late stent thrombosis. The transverse IVUS image 420 still further includes substantially strong ultrasound reflections from the stent struts 434 as well as so-called stent blooming artifacts 436. The stent blooming artifacts can result from saturation of the receive-side electronics that are part of the IVUS system and characteristically appear on the side of the stent struts 434 away from the catheter mask 422. The combined thickness of the stent reflection 434 and stent blooming artifact 436 is generally substantially larger than the physical thickness of the stent struts, which is approximately 100 microns or smaller. The stent blooming artifacts 436 degrade image quality.

Figure 22:
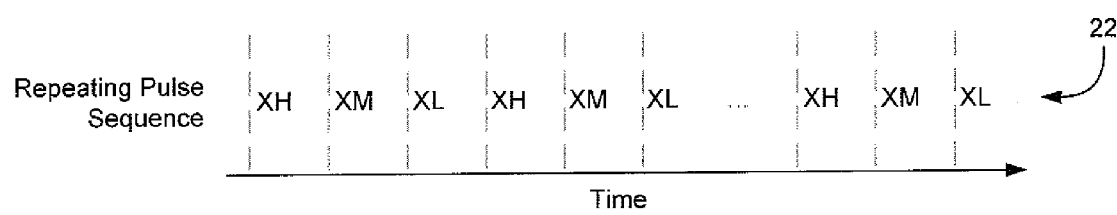
FIG. 22 illustrates a repeating high-energy, medium-energy, and low-energy transmit pulse sequence.

Stent blooming artifacts can be prevented by sufficiently decreasing the energy of the transmit pulse to avoid saturation of the receive-side electronics of the IVUS system. In one embodiment of the present invention, a three-pulse sequence that includes a high-transmit energy pulse, a medium-transmit energy pulse, and a low-transmit energy pulse may be used to visualize neotissue growth, provide adequate penetration of the ultrasound energy into the coronary artery, and prevent stent blooming artifacts. FIG. 22 illustrates a repeating pulse sequence 22 of high-energy transmit pulses XH, medium-energy transmit pulses XM, and low-energy transmit pulses XL.

The transverse IVUS image 420 shown in FIG. 21 is acquired with a high-transmit energy pulse and enables visualization of neotissue growth and penetration beyond the medial layer 430. FIG. 23 shows a transverse IVUS image 440 of the same stented coronary artery shown in FIG. 21, but acquired with a medium-transmit energy pulse having an amplitude less than the amplitude of the high-transmit energy pulse. The transverse IVUS image 440 includes a catheter mask 422 to indicate position of the IVUS catheter relative to the coronary artery. The IVUS image 440 further shows ultrasound reflections from a blood-filled lumen 424, neotissue growth 426, and an intimal plaque layer 428. The transverse IVUS image 440 still further includes ultrasound reflections from the stent struts 442 and stent blooming artifacts 444.

FIG. 24 shows a transverse IVUS image 450 of the same stented coronary artery shown in FIG. 21, but acquired with a low-transmit energy pulse having an amplitude less than the amplitude of the high-transmit energy pulse. The transverse IVUS image 450 includes a catheter mask 422 to indicate position of the IVUS catheter relative to the coronary artery. The IVUS image 440 further shows ultrasound reflections from neotissue growth 426 and parts of the intimal plaque layer 428. The transverse IVUS image 440 still further includes ultrasound reflections from the stent struts 454. Because of the low-transmit energy level of the pulse, there will be no stent blooming artifact and more distant sections of the coronary artery such as the medial and adventitial layers may not be visualized. The low-transmit energy level of the pulse may degrade the ability to detect and visualize the small ultrasound reflections from a blood-filled lumen.

Figure 25:
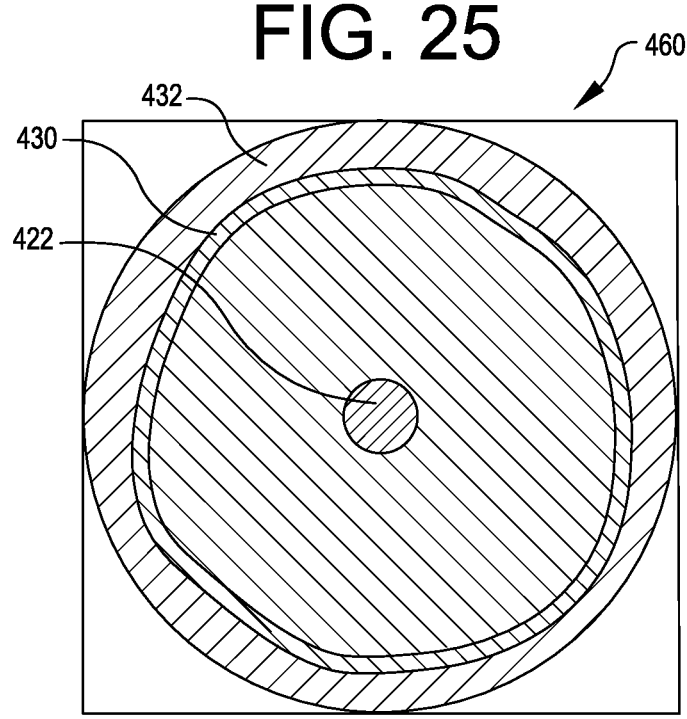
FIG. 25 shows a transverse IVUS image with a selected dynamic range of a stented coronary artery acquired using a high-transmit energy pulse.
Figure 26:
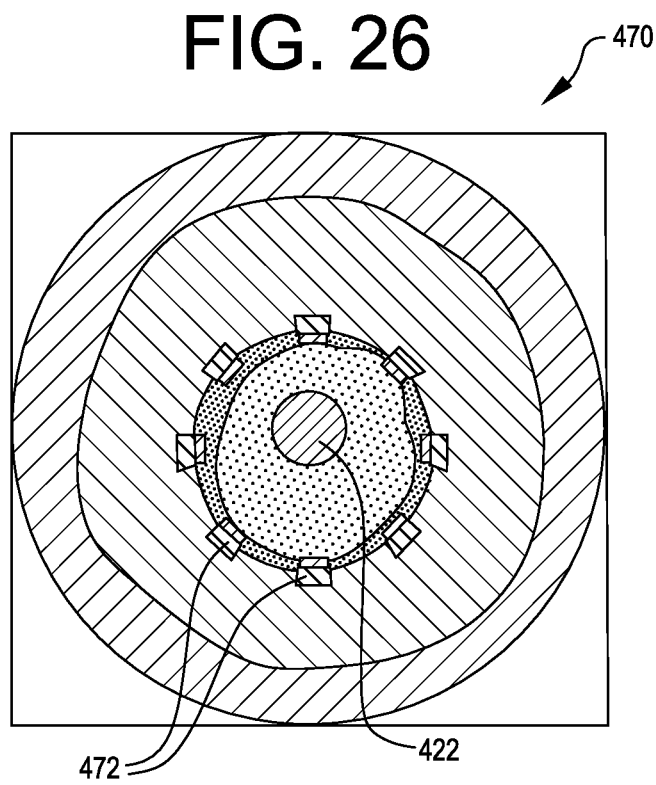
FIG. 26 shows a transverse IVUS image with a selected dynamic range of a stented coronary artery acquired using a medium-transmit energy pulse.
Figure 27:
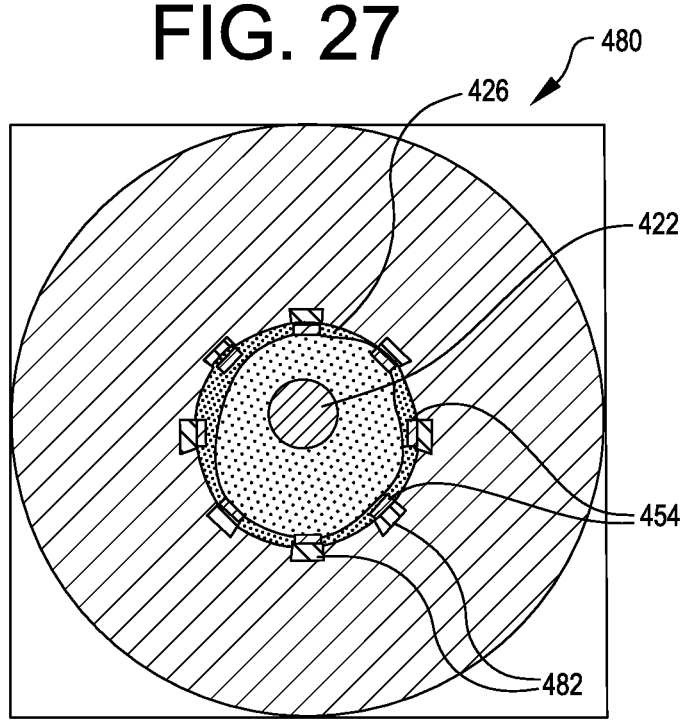
FIG. 27 shows the stent regions of a transverse IVUS image with a selected dynamic range of a stented coronary artery acquired using a low-transmit energy pulse.
Figure 28:
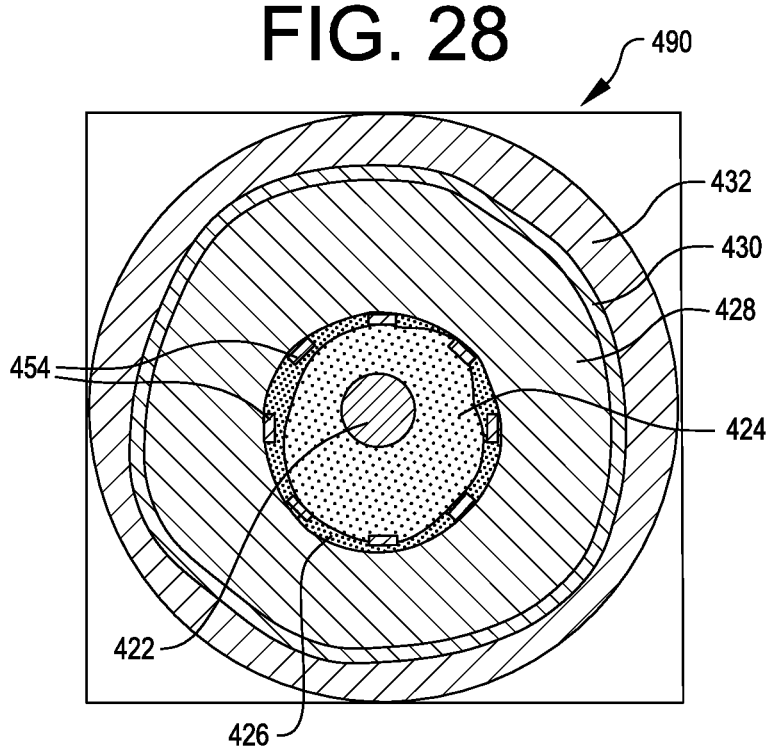
FIG. 28 shows a composite image of a high-transmit energy transverse IVUS image of a stented coronary artery, a medium-transmit energy transverse IVUS image of a stented coronary artery, and a low-transmit energy transverse IVUS image of a stented coronary artery.

A high-transmit energy IVUS image, a medium-transmit energy IVUS image, and a low-transmit energy IVUS image can be co-registered by using a sequence of repeated high-transmit energy, medium-transmit energy and low-transmit energy pulses. Referring now to FIG. 25, a high-transmit energy IVUS image 460 can be further processed to include deeper tissues that are visualized with a high-transmit energy pulse such as the medial layer 430 and the adventitia 432. Referring now to FIG. 26, a medium-transmit energy IVUS image 470 can be further processed to have sections 472 of the image that include the stents and stent blooming artifacts removed from the image. Referring now to FIG. 27, a low-transmit energy IVUS image 480 can be further processed to include the neotissue growth 426 and only those sections 454,472 that map to the sections of the medium-transmit energy IVUS image 470 that include the stents and stent blooming artifacts 472. Referring now to FIG. 28, the further processed high-transmit energy IVUS image 460 the further processed medium-transmit energy IVUS image 470, and the further processed low-transmit energy IVUS image 480 can be combined into a composite image 490 that visualizes neotissue growth 426 over stent struts 454, visualizes tissue beyond and including the medial layer 430, and avoids stent blooming artifacts.

Figure 29:
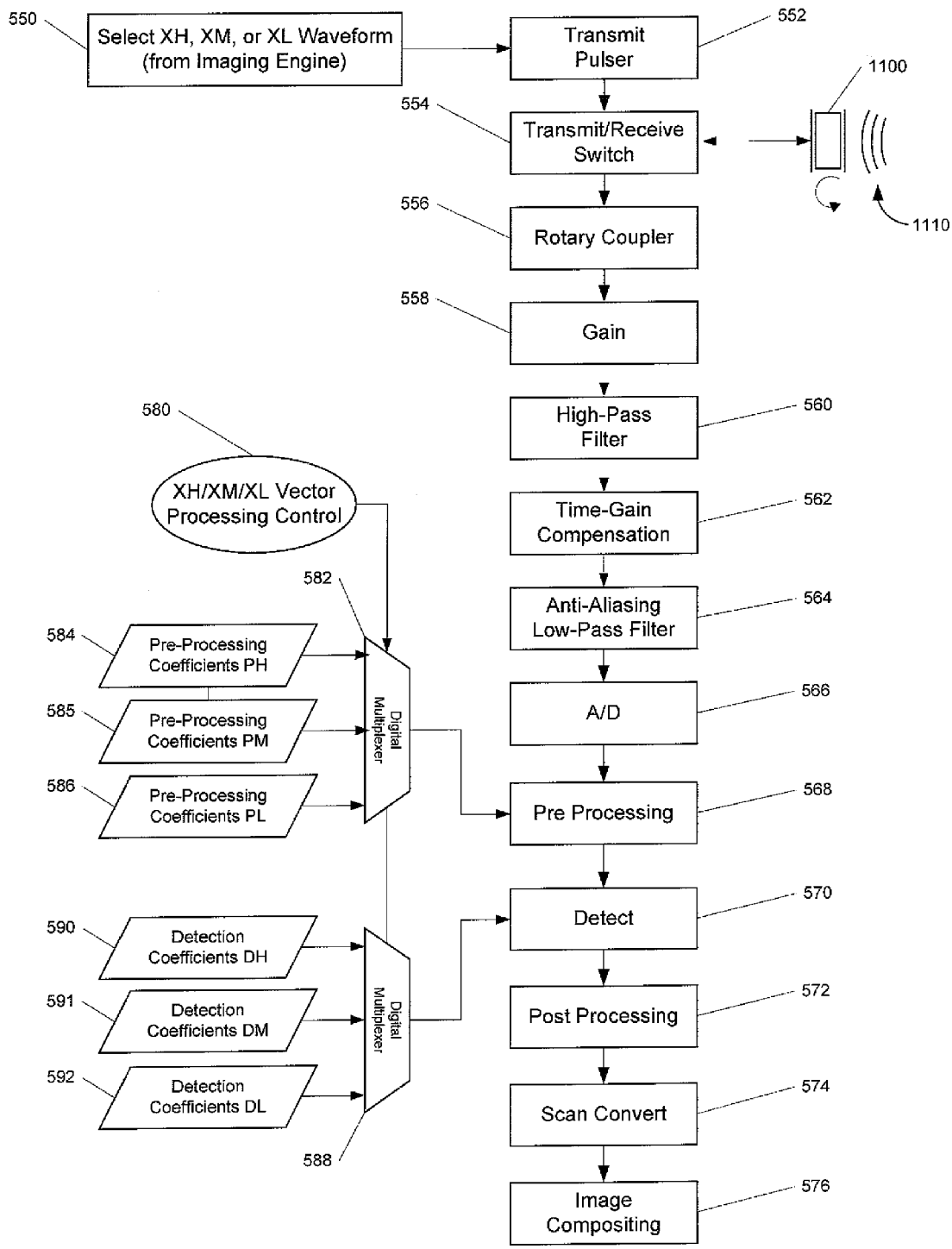
FIG. 29 is a flow diagram of the signal processing path of an IVUS system for imaging with a high-transmit, medium-transmit and low-transmit energy pulse sequence.

FIG. 29 illustrates one embodiment of a signal processing path generating a composite image from images acquired using high-transmit, medium-transmit, and low-transmit energy pulses. The following descriptions are directed to the case of an transmit pulse sequence 22 as illustrated in FIG. 22 wherein a first pulse XH has a high-transmit energy, a second pulse XM has a medium-transmit energy, and a third pulse XL has a low-transmit energy.

A high-transmit energy, medium-transmit energy, or low-transmit energy waveform, generally stored within an imaging engine, is selected in step 550. A transmit waveform is then generated by a transmit pulser in step 552. The transmit waveform is sent through a transmit/receive (T/R) switch in step 554 to an ultrasound transducer 1100. The transducer may operate over frequency ranges of 10 MHz to 80 MHz, generally between 20 MHz and 60 MHz for intracoronary imaging.

The transducer emits an ultrasonic pressure field 1110 to insonify the coronary artery. Some ultrasonic energy is backscattered and received by the transducer. The received ultrasound passes through the T/R switch in step 554 and a rotary coupler in step 556. The rotary coupler may be an inductive rotary coupler or a liquid metal rotary coupler. The rotary coupler interfaces the mechanically rotating imaging core of the catheter to the non-rotating electronics of the patient interface module.

Gain is then applied to the received signal in step 558. A high-pass filter is next applied to the amplified signal in step 560. A time-varying gain is applied to the high-pass filtered signal in step 562. The time-gain compensation is provided, because of the increased attenuation of the ultrasound signal as the signal propagates further into the coronary artery. An anti-aliasing low-pass filter is next applied to the signal in step 564 before the signal is digitized in step 566.

The digitized signals are pre-processed in step 568 wherein pre-processing generally includes band-pass filtering and vector processing techniques. The specific form of pre-processing depends on whether the transmit signal is a high-transmit energy pulse XH or a low-transmit energy pulse XL. A digital multiplexer 584 receives a first set of pre-processing coefficients PH 584, a second set of pre-processing coefficients PM 585, and a third set of pre-processing coefficients PL 586. The pre-processing coefficients include filter coefficients for band-pass filtering. A vector processing control 580 determines which set of pre-processing coefficients to use for pre-processing. The envelope of the pre-processed signal is detected in step 570. The vector processing control 580 determines whether a digital multiplexer 588 selects a first set of detection coefficients DH 590, a second set of detection coefficients DM 585, or a third set of detection coefficients DL 592 for detection processing. The detected signal is then post-processed in step 572 wherein post-processing generally includes logarithmic compression and gamma correction to generate a visually appealing and useful image.

The post-processed signals can then be scan converted from polar coordinates to Cartesian coordinates in step 574. The high-transmit energy, medium-transmit energy, and low-energy transmit scan-converted images are then combined into a composite image in step 576. The combination or fusion of the three images into a single composite image are achieved by selecting a portion of the dynamic range of each individual image. The composite image may then have a wider dynamic range than any single image. The composite image may then be compressed to satisfy parameters of the display device. The composite image includes neotissue growth over stent struts and tissue beyond and including the medial layer. The composite image further avoids stent blooming artifacts. The individual high-transmit energy, medium-transmit energy, and low-transmit energy images can be first aligned during post-processing to minimize motion artifacts. In addition, the images can be acquired during a period of relatively little motion, such as end diastole of the cardiac cycle, to further minimize motion artifacts. Motion artifacts can be further minimized by minimizing the depth or range of acquired data in order to minimize time between pulse transmissions.

While particular embodiments of the present invention have been shown and described, modifications may be made, and it is therefore intended to cover in the appended claims all such changes and modifications which fall within the true spirit and scope of the invention.

What is claimed is:

1. An intravascular ultrasound imaging system, comprising:
    a catheter having an elongated body having a distal end, the catheter having an imaging core configured to be inserted into the elongated body, the imaging core being configured to transmit ultrasonic energy pulses and to receive reflected ultrasonic energy pulses; and
    an imaging engine coupled to the imaging core and configured to provide the imaging core with energy pulses, the energy pulses being ultrasonic, to cause the imaging core to transmit the ultrasonic energy pulses, each energy pulse having a predefined energy pulse characteristic within a plurality of predefined energy pulse characteristics, the energy pulses being transmitted such that the associated predefined energy pulse characteristics are arranged in a repeating sequence, wherein
    the imaging engine is further configured to process the reflected ultrasonic energy pulses into separate image frames, the separate image frames being acquired from the sequence of predefined energy pulse characteristics of the reflected ultrasonic energy pulses, each image frame corresponding to a predefined energy pulse characteristic, the imaging engine being further configured to identify prominent features of each separate image frame, the imaging engine being configured to provide display signals for simultaneously displaying the separate image frames as a composite image, the imaging engine is further configured to form the composite image by co-registering the separate image frames, such that features more prominent in a first image of the separate image frames are mapped to a second image of the separate image frames, and features more prominent in the second image are mapped to the first image, thereby including at least a portion of the prominent features of each of the separate image frames in the composite image.

2. The system of claim 1, wherein the imaging engine is further configured to provide the imaging core with repeated sequence of energy pulses such that each sequence of energy pulses includes at least two pulses.

3. The system of claim 1, wherein the imaging engine is further configured to provide the imaging core with repeated sequence of energy pulses, such that the energy pulses in each sequence having a different pulse energy.

4. The system of claim 1, wherein the imaging engine is further configured to provide the imaging core with repeated sequence of energy pulses, such that the energy pulses in each sequence having a different frequency.

5. The system of claim 1, wherein the imaging engine is further configured to provide the imaging core with repeated sequence of energy pulses, such that the energy pulses in each sequence having a different bandwidth.

6. The system of claim 1, wherein the imaging engine is further configured to provide the imaging core with repeated sequence of energy pulses such that each sequence of energy pulses includes three pulses.

7. The system of claim 6, wherein the imaging engine is further configured to provide the imaging core with repeated sequence of energy pulses such that
    a first one of the three pulses has a first energy,
    a second one of the three pulses has a second energy, a third one of the three pulses has a third energy, wherein, the first energy is greater than the second energy, and the first energy is greater than the third energy.

8. The system of claim 1, wherein the imaging engine includes a processor configured to process the reflected ultrasonic energy pulses in image frames and a detector that detects the varying characteristic in the reflected ultrasonic energy pulses, and wherein the imaging engine processes the frames according to the detected varying characteristic.

9. The system of claim 8, wherein the imaging engine is further configured to process only reflected ultrasonic energy pulses having a common detected characteristic.

10. The system of claim 8, wherein the imaging engine is further configured to provide a composite image based upon the varying characteristics of the sequences of reflected ultrasonic energy pulses.

11. A method comprising:
    providing a catheter having an elongated body having a distal end and an imaging core configured to be inserted into the elongated body, the imaging core being configured to transmit ultrasonic energy pulses and to receive reflected ultrasonic energy pulses, an imaging engine coupled to the imaging core; and
    providing the imaging core with energy pulses from an imaging engine coupled to the imaging core, the energy pulses being ultrasonic, to cause the imaging core to transmit the ultrasonic energy pulses, each energy pulse having a predefined energy pulse characteristic within a plurality of predefined energy pulse characteristics, the energy pulses being transmitted such that the associated predefined energy pulse characteristics are arranged in a repeating sequence, wherein
the imaging engine processes the reflected ultrasonic energy pulses in separate image frames, the separate image frames being acquired concurrently from the reflected ultrasonic energy pulses, each image frame corresponding to a predefined energy pulse characteristic, and wherein the imaging engine provides display signals for simultaneously displaying the separate image frames as a composite image, the imaging engine identifies prominent features of each separate image frame and forms the composite image by co-registering the separate image frames, such that features more prominent in a first image of the separate image frames are mapped to a second image of the separate image frames, and features more prominent in the second image are mapped to the first image, thereby including at least a portion of the prominent features of each of the separate image frames in the composite image.

* * * * *